US008263088B2

(12) United States Patent
Moore et al.

(10) Patent No.: US 8,263,088 B2
(45) Date of Patent: Sep. 11, 2012

(54) CLOSTRIDIAL TOXIN NETB

(75) Inventors: Robert John Moore, Ascot Vale (AU); Julian Ian Rood, Bentleigh (AU); Anthony Leslie Keyburn, Leopold (AU)

(73) Assignee: Australian Poultry CRC Pty Ltd., Armidale, NSW (AU)

( * ) Notice: Subject to any disclaimer, the term of this patent is extended or adjusted under 35 U.S.C. 154(b) by 0 days.

(21) Appl. No.: 12/663,215

(22) PCT Filed: Jun. 6, 2008

(86) PCT No.: PCT/AU2008/000813
§ 371 (c)(1),
(2), (4) Date: Jun. 4, 2010

(87) PCT Pub. No.: WO2008/148166
PCT Pub. Date: Dec. 11, 2008

(65) Prior Publication Data
US 2010/0291131 A1    Nov. 18, 2010

Related U.S. Application Data

(60) Provisional application No. 60/942,858, filed on Jun. 8, 2007.

(51) Int. Cl.
*A61K 39/08* (2006.01)
(52) U.S. Cl. ............... 424/247.1; 424/185.1; 424/190.1; 530/300; 530/350
(58) Field of Classification Search .................. None
See application file for complete search history.

(56) References Cited

U.S. PATENT DOCUMENTS

| | | |
|---|---|---|
| 6,610,300 B1 | 8/2003 | Segers et al. |
| 2007/0243199 A1 | 10/2007 | Doelling et al. |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
Steinpórsdóttir, et al., "Expression and Purification of *Clostridium perfringens* Beta-Toxin Glutathione S-Transferase Fusion Protein," FEMS Mircobiology Letters, 130 (1995) pp. 273-278.
GenBank Accession No. ABW71134; Sep. 7, 2007 "Necrotic enteritis toxin B precursor (*Clostridium perfringens*)".
GenBank Accession No. EU143239; Sep. 7, 2007 "*Clostridium perfringens* necrotic enteritis toxin B precursor (NetB)".
GenBank Accession No. AAA23284; Oct. 29, 1993 "Beta-toxin".
GenBank Accession No. CAA58246; Apr. 18, 2005 "Beta-toxin (*Clostridium perfringens*)".
Bettelheim et al. "The Primary Structure of Proteins" in *Introduction to General Organic and Biochemistry*, Sixth Edition, pp. 509-511 (Chapter 21, 7), Harcourt College Publishers.
Hunter et al.; "Molecular genetic analysis of beta-toxin of *Clostridium perfringens* reveals sequence homology with alpha-toxin, gamma-toxin, and leukocidin of *Staphylococcus aureus*"; *Infection and Immunity*; 61(9): 3958-3965 (1993).
Waldman et al.; "Influence of a glycine or praline substitution on the functional properties of a 14-amino-acid analog of *Escherichia coli* heat-stable enterotoxin"; *Infection and Immunity*; 57(8): 2420-2424 (1989).
Logan et al., "Epitope Mapping of the Alpha-Toxin of *Clostridium perfringens*," Infection and Immunity, vol. 50, No. 12, Dec. 1991, pp. 4338-4342.
Williamson et al., "A Genetically Engineered Vaccine Against the Alpha-Toxin of *Clostridium perfringens* Protects Mice Against Experimental Gas Gangrene," Vaccine, vol. 11, Issue 12, 1992, pp. 1253-1258.
Titball, et al., "Biochemical and Immunological Properties of the C-Terminal Domain of the Alpha-Toxin of *Clostridium perfringens*," FEMS Microbiology Letters, 110 (1993), pp. 45-50.
Walker et al., "Key Residues for Membrane binding, Oligomerization and Pore Forming Activity by *Staphylococcal* α-Hemolysin Identified by Cysteine Scanning Mutagenesis and Targeted Chemical Modification," The Journal of Biological Chemistry, vol. 270, Sep. 29, 1995, pp. 23065-23071.
Steinthorsdottir et al., "Site-Directed Mutagenisis of *Clostridium perfringens* Beta-Toxin: Expression of Wild-type and Mutant Toxins in *Bacillus subtilis*" FEMS Microbiology Letters 158 (1998) pp. 17-23.
Song et al., "Structure of *Staphylococcal* α-Hemolysin, a Heptameric Transmembrane Pore," science, vol. 274, Dec. 13, 1996, pp. 1859-1866.
Database EMBL Sequence Archive, accession No. AJ252315, 2 pages, accessed Apr. 26, 2012.
Database EMBL Sequence Archive, accession No. EU143239, 2 pages, accessed Apr. 26, 2012.
Database EMBL Sequence Archive, accession No. L13198, 2 pages, accessed Apr. 26, 2012.
Keyburn, et al. "Alpha-Toxin of *Colstridium perfringens* Is Not an Essential Virulence Factor in Necrotic Enteritis in Chickens," *Infection and Immunity*, vol. 74(11), pp. 6496-6500 (Nov. 2006).
Keyburn, et al., "NetB, a New Toxin That Is Associated with Avian Necrotic Enteritis Caused by *Clostridium perfringens*," PLoS Pathogens, vol. 4(2), E26 (Feb. 2008).
Australian Office Action for Application No. 2008258277, 3 pages, dated Apr. 12, 2012.
Mexican Office Action for Application No. MX/a/2009/012924, 2 pages, dated Oct. 6, 2011.
Russian Office Action for Application No. 2009149378, 6 pages, dated Mar. 30, 2011.
Supplementary European Search Report for EP 08 75 6897, 6 pages, dated Sep. 23, 2011.

\* cited by examiner

*Primary Examiner* — Jennifer Graser
(74) *Attorney, Agent, or Firm* — Kilpatrick Townsend & Stockton LLP

(57) ABSTRACT

The present invention relates to a polypeptide based toxin that originates from *Clostridium perfringens*. The invention further relates to immunogenic compositions comprising the toxin and methods to vaccinate animals, for example chickens, such that they are less susceptible to clostridial diseases. Methods to determine whether an animal has been exposed to the toxin, polynucleotides encoding the toxin and attenuated bacteria that express a reduced or less active form of the toxin are also disclosed.

9 Claims, 8 Drawing Sheets

Figure 2:
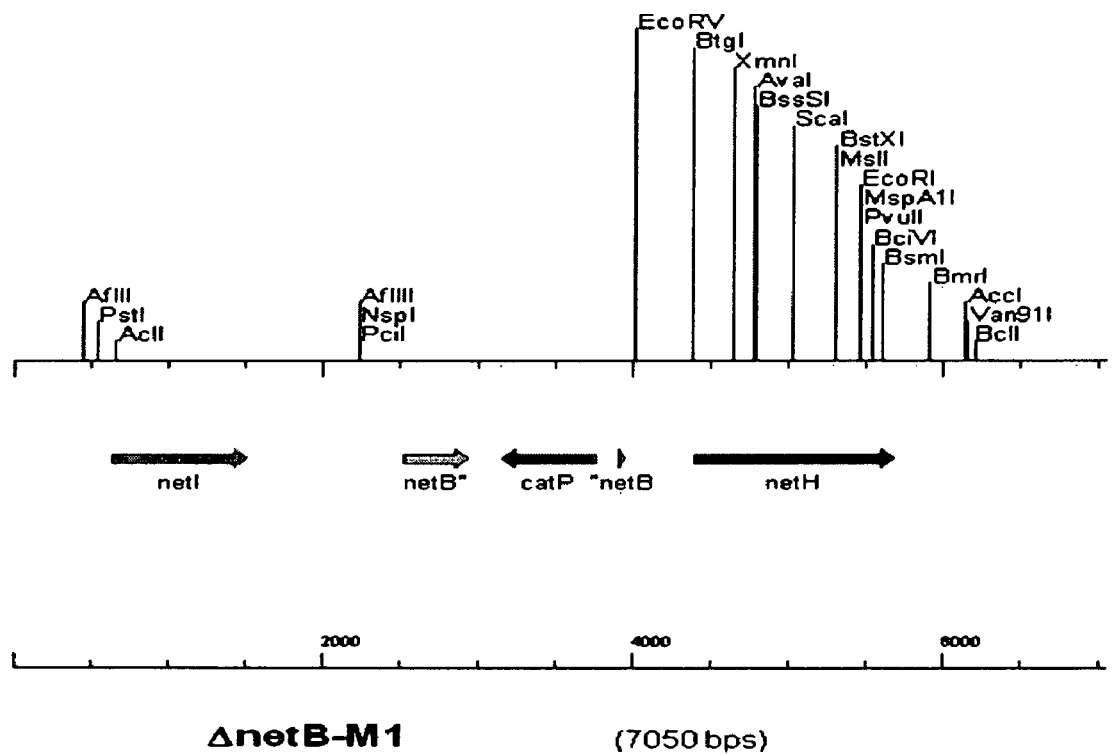

```
netB       = (SEQ ID NO:3)
beta-toxin = (SEQ ID NO:4)

netB        YYKGGIILKRLKIISITLVLTSVISTSLFSTQTQVFASELNDINKIELKNLSG--EIIKE  58
beta-toxin  ---------MKKKFISLVIVSSLLNGCLLSPTLVYANDIGKTTTITRNKTSDGYTIITQ  50
                 :*    *:**:.*  :  ..  :  : * *:*.::..  ..*   ::  *.    **.:

netB        NGKEAIKYTSSDTAS--HKGWKATLSGTFIEDPHSDKKTALLNLEGFIPSDKQIFGSKY- 115
beta-toxin  NDKQIISYQSVDSSSKNEDGFTASIDARFIDDKYSSEMTTLINLTGFMSSKKEDVIKKYN 110
            *.*: *.* * *::*  ..*:.*::..  **:*  :*.:  *:*:** **:.*.*:  . .**

netB        ------YGKMKWPETYRINVKSADVNNNIKIANSIPKNTIDKKDVSNSIGYSIGGNISVE 169
beta-toxin  LHDVTNSTAINFPVRYSISILNESINENVKIVDSIPKNTISQKTVSNTMGYKIGGSIEIE 170
                  :::*   *  *.:  .  .:*:*:,:*****.:*  *:..***.*.:* netB        GKTAGAGINASYNVQNTISYEQPDFRTIQRKDDANLASWDIKFVETKDG-YNIDSYHAIY 228
beta-toxin  KNKPKASIESEYAESSTIEYVQPDFSTIQTDHSTSKASWDTKFTETTRGNYNLKSNNPVY 230
            :..  *.*::.*  ..**.*  ** *  ...:.  ** .**.  * **:.*  :.:* netB        GNQLFMKSRLYNN-GDKNFTDDRDLSTLISGGFSPNMALALTAPKNAKESVIIVEYQRFD 287
beta-toxin  GNEMFMYGRYTNVPATENIIPDYQMSKLITGGLNPNMSVVLTAPNGTEESIIKVKMERER 290
            ::  .*  *    .  :*:    *  ;:*.:::.*::.:..:::* *:  :* netB        NDYILNWETTQWRG--TNKLSSTS---EYNEFMFKINWQDHKIEYYL 329
beta-toxin  NCYYLNWNGANWVGQVYSRLAFDTPNVDSHIFTFKINWLTHKVTAI- 336
            * * ***: ::* *    .:*:  :     :  : * ***** **:
```

Figure 1

SEQUENCE LISTING

<160> NUMBER OF SEQ ID NOS: 10

<210> SEQ ID NO 1
<211> LENGTH: 1320
<212> TYPE: DNA
<213> ORGANISM: Clostridium perfringens

<400> SEQUENCE: 1

```
atcattttac aagtttaact tgattattac ttattttttgc ataaatttta ataaaattta      60
tgcaaaaata gaatttaaaa tagattttta taatttttta taaattaaga atactaaaca     120
aaaaaccagt tatgtataaa ttttgaccag ttttaccaaa gttattgaaa atatcaaata     180
aacaagtgat aataactata ataatattat aaaggaggaa ttattttgaa agattaaaa      240
attatttcaa ttacactagt tcttacaagt gtaattagta caagcctttt ttcaactcaa     300
actcaagttt tgcaagtga attaaatgac ataaacaaaa ttgagttgaa aaatctaagt      360
ggagaaataa taaagaaaa tggaaaggaa gctattaaat atacttctag tgataccgct      420
tcacataaag gttggaaggc aactttaagt ggaacattta ttgaagatcc tcattctgat     480
aagaaaactg ctttattaaa tttagaagga tttatacctt ctgataaaca gattttttggt    540
tctaaatatt acggaaaaat gaatggcct gaaacttata gaattaatgt aaaaagtgct      600
gatgtaaata ataatataaa aatagcaaat tctattccta aaaatactat agataaaaaa    660
gatgtatcta attcaattgg ttattctata ggcggtaata tatctgttga aggaaaaact     720
gctggtgctg gaataaatgc ttcatataat gtccaaaata ctataagcta tgaacaacct     780
gattttagaa caattcaaag aaaagatgat gcaaatttag catcatggga tataaaattt     840
gttgagacta aggacggtta ataatatagat tcttatcatg ctatttatgg aaatcaatta    900
ttcatgaaat caagattgta taataatggt gataaaaatt tcacagatga tagagattta    960
tcaacattaa tttctggtgg attttcaccc aatatggctt tagcattaac agcacctaaa   1020
aatgctaaag aatctgtaat aatagttgaa tatcaaagat ttgataatga ctatatttta   1080
aattgggaaa ctactcaatg gcgaggaaca aacaaacttt cgtcaacaag tgaatataac    1140
gaatttatgt ttaaaataaa ttggcaagat cataaaatag aatattatct gtaatttaat   1200
attttatttt tataagtttg attaatttac atatgattt gatttcttac aagttaatca    1260
aagatatcaa taaataaatt gtttttatta gaataatcat taatattaaa attggacaat   1320
```

<210> SEQ ID NO 2
<211> LENGTH: 292
<212> TYPE: PRT
<213> ORGANISM: Clostridium perfringens

<400> SEQUENCE: 2

```
Ser Glu Leu Asn Asp Ile Asn Lys Ile Glu Leu Lys Asn Leu Ser Gly
 1               5                  10                  15

Glu Ile Ile Lys Glu Asn Gly Lys Glu Ala Ile Lys Tyr Thr Ser Ser
                20                  25                  30

Asp Thr Ala Ser His Lys Gly Trp Lys Ala Thr Leu Ser Gly Thr Phe
            35                  40                  45

Ile Glu Asp Pro His Ser Asp Lys Lys Thr Ala Leu Leu Asn Leu Glu
        50                  55                  60

Gly Phe Ile Pro Ser Asp Lys Gln Ile Phe Gly Ser Lys Tyr Tyr Gly
    65                  70                  75                  80

Lys Met Lys Trp Pro Glu Thr Tyr Arg Ile Asn Val Lys Ser Ala Asp
```

```
                85                  90                  95
Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
            115                 120                 125

Ile Ser Val Glu Gly Lys Thr Ala Gly Ala Gly Ile Asn Ala Ser Tyr
        130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
            195                 200                 205

Phe Thr Asp Asp Arg Asp Leu Ser Thr Leu Ile Ser Gly Gly Phe Ser
        210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255

Trp Glu Thr Thr Gln Trp Arg Gly Thr Asn Lys Leu Ser Thr Ser
            260                 265                 270

Glu Tyr Asn Glu Phe Met Phe Lys Ile Asn Trp Gln Asp His Lys Ile
            275                 280                 285

Glu Tyr Tyr Leu
        290

<210> SEQ ID NO 3
<211> LENGTH: 329
<212> TYPE: PRT
<213> ORGANISM: Clostridium perfringens

<400> SEQUENCE: 3

Tyr Tyr Lys Gly Gly Ile Ile Leu Lys Arg Leu Lys Ile Ile Ser Ile
1               5                   10                  15

Thr Leu Val Leu Thr Ser Val Ile Ser Thr Ser Leu Phe Ser Thr Gln
            20                  25                  30

Thr Gln Val Phe Ala Ser Glu Leu Asn Asp Ile Asn Lys Ile Glu Leu
        35                  40                  45

Lys Asn Leu Ser Gly Glu Ile Ile Lys Glu Asn Gly Lys Glu Ala Ile
    50                  55                  60

Lys Tyr Thr Ser Ser Asp Thr Ala Ser His Lys Gly Trp Lys Ala Thr
65                  70                  75                  80

Leu Ser Gly Thr Phe Ile Glu Asp Pro His Ser Asp Lys Lys Thr Ala
                85                  90                  95

Leu Leu Asn Leu Glu Gly Phe Ile Pro Ser Asp Lys Gln Ile Phe Gly
            100                 105                 110

Ser Lys Tyr Tyr Gly Lys Met Lys Trp Pro Glu Thr Tyr Arg Ile Asn
        115                 120                 125

Val Lys Ser Ala Asp Val Asn Asn Ile Lys Ile Ala Asn Ser Ile
    130                 135                 140

Pro Lys Asn Thr Ile Asp Lys Lys Asp Val Ser Asn Ser Ile Gly Tyr
145                 150                 155                 160

Ser Ile Gly Gly Asn Ile Ser Val Glu Gly Lys Thr Ala Gly Ala Gly
```

```
                165                 170                 175
Ile Asn Ala Ser Tyr Asn Val Gln Asn Thr Ile Ser Tyr Glu Gln Pro
            180                 185                 190

Asp Phe Arg Thr Ile Gln Arg Lys Asp Asp Ala Asn Leu Ala Ser Trp
        195                 200                 205

Asp Ile Lys Phe Val Glu Thr Lys Asp Gly Tyr Asn Ile Asp Ser Tyr
    210                 215                 220

His Ala Ile Tyr Gly Asn Gln Leu Phe Met Lys Ser Arg Leu Tyr Asn
225                 230                 235                 240

Asn Gly Asp Lys Asn Phe Thr Asp Asp Arg Asp Leu Ser Thr Leu Ile
                245                 250                 255

Ser Gly Gly Phe Ser Pro Asn Met Ala Leu Ala Leu Thr Ala Pro Lys
            260                 265                 270

Asn Ala Lys Glu Ser Val Ile Ile Val Glu Tyr Gln Arg Phe Asp Asn
        275                 280                 285

Asp Tyr Ile Leu Asn Trp Glu Thr Thr Gln Trp Arg Gly Thr Asn Lys
    290                 295                 300

Leu Ser Ser Thr Ser Glu Tyr Asn Glu Phe Met Phe Lys Ile Asn Trp
305                 310                 315                 320

Gln Asp His Lys Ile Glu Tyr Tyr Leu
                325

<210> SEQ ID NO 4
<211> LENGTH: 336
<212> TYPE: PRT
<213> ORGANISM: Clostridium perfringens

<400> SEQUENCE: 4

Met Lys Lys Lys Phe Ile Ser Leu Val Ile Val Ser Ser Leu Leu Asn
1               5                   10                  15

Gly Cys Leu Leu Ser Pro Thr Leu Val Tyr Ala Asn Asp Ile Gly Lys
            20                  25                  30

Thr Thr Thr Ile Thr Arg Asn Lys Thr Ser Asp Gly Tyr Thr Ile Ile
        35                  40                  45

Thr Gln Asn Asp Lys Gln Ile Ile Ser Tyr Gln Ser Val Asp Ser Ser
    50                  55                  60

Ser Lys Asn Glu Asp Gly Phe Thr Ala Ser Ile Asp Ala Arg Phe Ile
65                  70                  75                  80

Asp Asp Lys Tyr Ser Ser Glu Met Thr Thr Leu Ile Asn Leu Thr Gly
                85                  90                  95

Phe Met Ser Ser Lys Lys Glu Asp Val Ile Lys Lys Tyr Asn Leu His
            100                 105                 110

Asp Val Thr Asn Ser Thr Ala Ile Asn Phe Pro Val Arg Tyr Ser Ile
        115                 120                 125

Ser Ile Leu Asn Glu Ser Ile Asn Glu Asn Val Lys Ile Val Asp Ser
    130                 135                 140

Ile Pro Lys Asn Thr Ile Ser Gln Lys Thr Val Ser Asn Thr Met Gly
145                 150                 155                 160

Tyr Lys Ile Gly Gly Ser Ile Glu Ile Glu Lys Asn Lys Pro Lys Ala
                165                 170                 175

Ser Ile Glu Ser Glu Tyr Ala Glu Ser Ser Thr Ile Glu Tyr Val Gln
            180                 185                 190

Pro Asp Phe Ser Thr Ile Gln Thr Asp His Ser Thr Ser Lys Ala Ser
        195                 200                 205

Trp Asp Thr Lys Phe Thr Glu Thr Thr Arg Gly Asn Tyr Asn Leu Lys
```

```
                    210                 215                 220
Ser Asn Asn Pro Val Tyr Gly Asn Glu Met Phe Met Tyr Gly Arg Tyr
225                 230                 235                 240

Thr Asn Val Pro Ala Thr Glu Asn Ile Ile Pro Asp Tyr Gln Met Ser
                245                 250                 255

Lys Leu Ile Thr Gly Gly Leu Asn Pro Asn Met Ser Val Val Leu Thr
                260                 265                 270

Ala Pro Asn Gly Thr Glu Glu Ser Ile Ile Lys Val Lys Met Glu Arg
                275                 280                 285

Glu Arg Asn Cys Tyr Tyr Leu Asn Trp Asn Gly Ala Asn Trp Val Gly
        290                 295                 300

Gln Val Tyr Ser Arg Leu Ala Phe Asp Thr Pro Asn Val Asp Ser His
305                 310                 315                 320

Ile Phe Thr Phe Lys Ile Asn Trp Leu Thr His Lys Val Thr Ala Ile
                325                 330                 335

<210> SEQ ID NO 5
<211> LENGTH: 20
<212> TYPE: DNA
<213> ORGANISM: Artificial
<220> FEATURE:
<223> OTHER INFORMATION: oligonucleotide primer

<400> SEQUENCE: 5
gctggtgctg gaataaatgc                                               20

<210> SEQ ID NO 6
<211> LENGTH: 20
<212> TYPE: DNA
<213> ORGANISM: Artificial
<220> FEATURE:
<223> OTHER INFORMATION: Oligonucleotide primer

<400> SEQUENCE: 6
tcgccattga gtagtttccc                                               20

<210> SEQ ID NO 7
<211> LENGTH: 26
<212> TYPE: DNA
<213> ORGANISM: Artificial
<220> FEATURE:
<223> OTHER INFORMATION: Oligonucleotide primer

<400> SEQUENCE: 7
gcaattggca agatcataaa atagaa                                        26

<210> SEQ ID NO 8
<211> LENGTH: 27
<212> TYPE: DNA
<213> ORGANISM: Artificial
<220> FEATURE:
<223> OTHER INFORMATION: Oligonucleotide primer

<400> SEQUENCE: 8
ccctaggtat tttcttatcg ctacttg                                       27

<210> SEQ ID NO 9
<211> LENGTH: 27
<212> TYPE: DNA
<213> ORGANISM: Artificial
<220> FEATURE:
<223> OTHER INFORMATION: Oligonucleotide primer

<400> SEQUENCE: 9
```

```
gggatccaat tgtaaacatt cctgata                                              27

<210> SEQ ID NO 10
<211> LENGTH: 31
<212> TYPE: DNA
<213> ORGANISM: Artificial
<220> FEATURE:
<223> OTHER INFORMATION: Oligonucleotide primer

<400> SEQUENCE: 10
agctagctat tattatttac atcagcactt t                                         31
```

CLOSTRIDIAL TOXIN NETB

CROSS-REFERENCE TO RELATED APPLICATIONS

This application is the U.S. National Stage entry under §371 of International Application No. PCT/AU2008/00813, filed Jun. 6, 2008, which claims priority to and benefit of provisional U.S. Patent Application No. 60/942,858, filed Jun. 8, 2007; the disclosures of each are herein incorporated by reference in their entirety.

FIELD OF THE INVENTION

The present invention relates to a novel toxin. The invention further relates to immunogenic compositions comprising the toxin and methods of vaccinating animals, for example chickens, such that they are less susceptible to clostridial diseases.

BACKGROUND OF THE INVENTION

The genus *Clostridium* consists of gram-positive, anaerobic, spore-forming bacilli. The natural habitat of these organisms is the environment and the intestinal tracts of humans and other animals. Despite the identification of approximately 100 species of *Clostridium*, only a small number have been recognized as etiologic agents of medical and veterinary importance. Nonetheless, these species are associated with serious diseases, including botulism, tetanus, anaerobic cellulitis, gas gangrene, bacteremia, pseudomembranous colitis, and clostridial gastroenteritis.

*Clostridium perfringens* is the etiological agent for numerous clostridial diseases found in economically valuable domestic animals. Necrotic enteritis (NE) is one example of a clostridial enteric disease caused by *C. perfringens*. Necrotic enteritis leads to the development of necrotic lesions in the gut wall resulting in morbidity and mortality of poultry. It is also a multifactoral disease with complex and partly unknown epidemiology and pathogenesis (Kaldhusdal, 1999). The bacterium, *C. perfringens* is commonly found in the gastrointestinal tract of poultry (Tschirdewahn et al., 1991), the occurrence of necrotic enteritis, however, is sporadic (Cowen et al., 1987). Nevertheless, feed contaminated with *C. perfringens* has been implicated in outbreaks of necrotic enteritis in chickens (Kaldhusdal, 1999). Studies have also shown that healthy chickens have a relatively low number of *C. perfringens* in their gastrointestinal tracts, while an increase in the concentration of the bacteria can result in a necrotic enteritis condition (Craven et al., 1999).

Clinical necrotic enteritis is thought to occur when *C. perfringens* proliferates to high numbers in the small intestine and produces extracellular toxins that damage the intestine. The major toxin believed to be involved is the alpha-toxin, but its precise role in the disease process is not completely understood. The alpha-toxin is a secreted zinc-metalloenzyme which has both phospholipase C and sphingomyelinase activity and is the major toxin involved in the pathogenesis of human gas gangrene (Awad, et al., 1995; Songer, 1997). All five toxin types of *C. perfringens* (A to E) carry and express the alpha-toxin structural gene, plc.

To date, no other toxin had been identified as an essential virulence factor in necrotic enteritis.

SUMMARY OF THE INVENTION

The present inventors have identified a novel clostridial toxin. The inventors have named this polypeptide NetB.

Accordingly, the present invention provides a substantially purified or recombinant polypeptide, wherein the polypeptide comprises:
  i) an amino acid sequence as provided in SEQ ID NO:2 or SEQ ID NO:3,
  ii) an amino acid sequence which is at least 40% identical to SEQ ID NO:2 and/or SEQ ID NO:3, or
  iii) a biologically active and/or antigenic fragment of i) or ii).

In one embodiment, the polypeptide has toxin activity.

In another embodiment, the polypeptide has reduced toxin activity compared to a polypeptide encoded by SEQ ID NO:2 and/or SEQ ID NO:3.

In a preferred embodiment, the polypeptide comprises an amino acid sequence which is at least 90% identical to SEQ ID NO:2 or SEQ ID NO:3.

In one embodiment, the polypeptide can be purified from a bacterium of the genus *Clostridium*. Preferably, the polypeptide can be purified from *Clostridium perfringens*.

In another embodiment of the present invention, the polypeptide is a toxoid.

In yet another embodiment, the polypeptide is a fusion protein comprising at least one other polypeptide sequence.

The at least one other polypeptide may be, for example, a polypeptide that enhances the stability of a polypeptide of the present invention, or a polypeptide that assists in the purification of the fusion protein, or a polypeptide that enhances the immunological properties of the polypeptide of the present invention.

In yet another embodiment, the polypeptide of the invention is a synthetic polypeptide.

The present invention further provides an isolated and/or recombinant polynucleotide comprising:
  i) a sequence of nucleotides as provided in SEQ ID NO:1,
  ii) a sequence of nucleotides encoding a polypeptide of any one of claims 1 to 8,
  iii) a sequence of nucleotides which is at least 40% identical to SEQ ID NO:1, and/or
  iv) a sequence which hybridises with any one of i) to iii) under stringent conditions or the reverse complement thereof.

In one embodiment, the isolated or recombinant polynucleotide comprises a sequence of nucleotides at least 40% identical to nucleotides 226 to 1194 of SEQ ID NO:1.

The present invention further provides a vector comprising the polynucleotide of the invention.

Preferably, the polynucleotide in the vector is operably linked to a promoter.

In one embodiment, the vector is a viral vector or a plasmid vector.

The present invention further provides a host cell comprising the polypeptide of the invention, the polynucleotide of the invention and/or the vector of the invention.

Host cells of the present invention can be any cell capable of producing at least one polypeptide of the present invention, and include animal, plant, bacterial, fungal (including yeast), parasite, and arthropod cells.

Preferably, the host cell is a bacterium.

In one embodiment, the bacterium is *E. coli*. In a more preferred embodiment, the bacterium is *E. coli* selected from CCEC22, CCEC31 and CCEC59.

The present invention further provides a method for producing a polypeptide according to the invention, the method comprising cultivating a host cell according to the invention, or a vector of the invention encoding said polypeptide, under conditions which allow expression of the polynucleotide encoding the polypeptide.

Preferably, the method further comprises isolating said polypeptide.

The present invention further provides a substantially purified antibody, or fragment thereof, that binds specifically to a polypeptide of the invention.

The present invention further provides a composition comprising the polypeptide of the invention, the polynucleotide of the invention, the vector of the invention, the host cell of the invention, and/or the antibody of the invention.

In one embodiment, the composition is an immunogenic composition.

In one embodiment, the immunogenic composition further comprises an adjuvant and/or pharmaceutically acceptable carrier.

The present invention further provides a vaccine comprising an antigen, wherein the antigen comprises a polypeptide according to the invention.

In an embodiment, the vaccine comprises an adjuvant and/or pharmaceutically acceptable carrier.

In one embodiment, the vaccine further comprises one or more additional antigens.

The present invention further provides a DNA vaccine comprising a polynucleotide encoding a polypeptide according to the invention, wherein upon administration to a subject the polypeptide is expressed and an immune response to the polypeptide is produced.

The present invention further provides an attenuated bacterium which produces a polypeptide comprising an amino acid sequence which is at least 40% identical to SEQ ID NO:2 and/or SEQ ID NO:3, wherein the bacterium produces a reduced amount of the polypeptide compared to a wild-type bacterium and/or has reduced toxin activity compared to the polypeptide in a wild-type bacterium.

In one embodiment, the attenuated bacterium does not express the polypeptide.

In another embodiment, the attenuated bacterium has been further modified to express a heterologous polypeptide. The heterologous polypeptide may be, for example, a biologically active polypeptide or an antigen. Examples of biologically active polypeptides include cytokines, growth factors and enzymes. The antigen may be from, for example, a bacterial, fungal, parasitic or viral disease agent.

Preferably, the attenuated bacterium belongs to the genus *Clostridium*. In a most preferred embodiment, the bacterium is *Clostridium perfringens*.

The present invention further provides a method of attenuating the virulence of a bacterium which expresses a polypeptide comprising an amino acid sequence at least 40% identical to SEQ ID NO:2 and/or SEQ ID NO:3, the method comprising mutating a polynucleotide sequence to reduce the expression and/or toxin activity of the polypeptide, whereby the attenuated bacterium has reduced toxin activity compared to the unattenuated bacterium.

The present invention further provides a method of raising an immune response in a subject, the method comprising administering to the subject the polypeptide of the invention, the polynucleotide of the invention, the vector of the invention, the composition of the invention, the vaccine of the invention, the host cell of the invention, and/or the bacterium of the invention.

In one embodiment, the host cell or bacterium is live.

In another embodiment, the polypeptide, polynucleotide, composition, vector, host cell or bacterium is delivered in ovo.

The present invention further provides a method of determining whether a subject has been exposed to a pathogen which expresses a polypeptide comprising an amino acid sequence which is at least 40% identical to SEQ ID NO:2 and/or SEQ ID NO:3, wherein the method comprises determining the presence or absence of the polypeptide in a sample obtained from the subject, wherein the presence of the polypeptide is indicative of exposure to the pathogen.

The present invention further provides a method of determining whether a subject has been exposed to a pathogen which expresses a polypeptide comprising an amino acid sequence which is at least 40% identical to SEQ ID NO:2 and/or SEQ ID NO:3, wherein the method comprises determining the presence or absence of antibodies in the sample which bind specifically to a polypeptide according to the invention, wherein the presence of the antibodies is indicative of exposure to the pathogen.

The present invention further provides a method of determining whether a subject has been exposed to a pathogen which expresses a polynucleotide comprising a sequence of nucleotides which is at least 40% identical to SEQ ID NO:1, wherein the method comprises determining the presence or absence of the polynucleotide in a sample obtained from the subject, wherein the presence of the polynucleotide is indicative of exposure to the pathogen.

Any suitable technique for determining the presence or absence of the polynucleotide may be used. For example, the presence or absence of the polynucleotide may be detected by hybridisation, for example by Southern blot, or by amplification of the polynucleotide, for example by PCR.

In one embodiment the pathogen is from the genus *Clostridium*. In a preferred embodiment, the pathogen is *Clostridium perfringens*.

In one embodiment of the methods of the invention, the subject is avian.

Preferably, the subject is poultry. For example the subject may be a chicken, turkey, pheasant, quail, duck, ostrich or other poultry commonly bred in commercial quantities.

In a most preferred embodiment, the subject is a chicken.

The present invention further provides a method of screening for an agonist or antagonist which modulates the activity of a polypeptide of the invention, the method comprising contacting the polypeptide of the invention with a candidate compound, and determining whether said compound increases or decreases the toxin activity of the polypeptide of the invention. In one embodiment, the compound is an antagonist. Preferably, the compound is an antibody.

The present invention further provides a method of testing a sample for toxin activity, the method comprising:

(a) dividing a sample suspected of containing a polypeptide according to any one of claims 1 to 8 into at least first and second subsamples, (b) contacting the first subsample with an antagonist of a polypeptide according to any one of claims 1 to 8, and (c) determining whether the first and second subsamples have toxin activity, wherein the absence of toxin activity in the first subsample and presence of toxin activity in the second sample is indicative of the presence of a polypeptide which is at least 40% identical to SEQ ID NO:2 and/or SEQ ID NO:3.

In one embodiment, step (c) comprises independently incubating the first and second subsamples with animal cells under conditions, and for a period, sufficient for the polypeptide to exert a cytopathic effect and determining the presence or absence of a cytopathic effect on the cells.

In a preferred embodiment, the antagonist is an antibody.

The present invention further provides feed and/or drink comprising an antagonist of the polypeptide according to the invention.

Preferably, the antagonist is an antibody according to the invention.

The present invention further provides use of the feed and/or drink of the invention to reduce infection and/or colonization of an animal by a bacteria which expresses a polypeptide comprising an amino acid sequence which is at least 40% identical to SEQ ID NO:2 and/or SEQ ID NO:3.

The present invention further provides a non-human transgenic organism comprising an exogenous polynucleotide encoding the polypeptide according to the invention. Preferably, the non-human transgenic organism is a plant.

The present invention further provides a feed and/or drink comprising the polypeptide of the invention.

Preferably, the polypeptide raises an immune response against a bacterial pathogen when the non-human transgenic organism and/or the feed and/or drink is administered orally to a subject. The bacterial pathogen may be of the genus *Clostridium*, for example, *Clostridium perfringens*. Preferably, the subject is avian, for example, a chicken, turkey or duck.

As would be understood by the skilled person, the non-human transgenic organism and/or the feed and/or drink of the invention could be used to administer the polypeptide of the invention to a subject, such that an immune response against the polypeptide is raised in the subject.

Thus, in one embodiment, the present invention provides a method of raising an immune response against the polypeptide of the invention, the method comprising orally administering to the subject the non-human transgenic organism of the invention and/or the feed and/or drink of the invention.

The present invention further provides a method of providing passive immunity to the progeny of a female avian, the method comprising administering the polypeptide of the invention, the polynucleotide of the invention, the vector of the invention, the host cell of the invention, the composition of the invention, the vaccine of the invention, the attenuated bacterium of the invention, the non-human transgenic organism of the invention, and/or the feed and/or drink of the invention to the female avian prior to the female avian laying eggs comprising the progeny, whereby the progeny are provided passive immunity to a bacteria that expresses a polypeptide comprising an amino acid sequence which is at least 40% identical to SEQ ID NO:2 and/or SEQ ID NO:3.

The present invention further provides use of the polypeptide of the invention, the polynucleotide of the invention, the vector of the invention, the composition of any the invention, the vaccine of the invention, the host cell of the invention, the bacterium of the invention, the non-human transgenic animal of the invention and/or the feed and/or drink of the invention in the manufacture of a medicament for raising an immune response in a subject.

The present invention further provides use of the polypeptide of the invention, the polynucleotide of the invention, the vector of the invention, the composition of the invention, the vaccine of the invention, the host cell of the invention, the bacterium of the invention, the non-human transgenic animal of the invention and/or the feed or drink of the invention as a medicament for raising an immune response in a subject.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. ClustalW alignment of NetB and beta-toxin from *C. perfringens*; "*" means that the residues or nucleotides in that column are identical in all sequences in the alignment; ":" means that conserved substitutions have been observed; "." means that semi-conserved substitutions are observed.

FIG. 2. Schematic diagram of NE18-ΔnetB chromosome region. The netB mutants were constructed by allelic exchange using a suicide plasmid containing an insertionally inactivated netB gene with approximately 2 kb of homologous DNA on either side of the gene and introduced into EHE-NE18.

Figure 3:
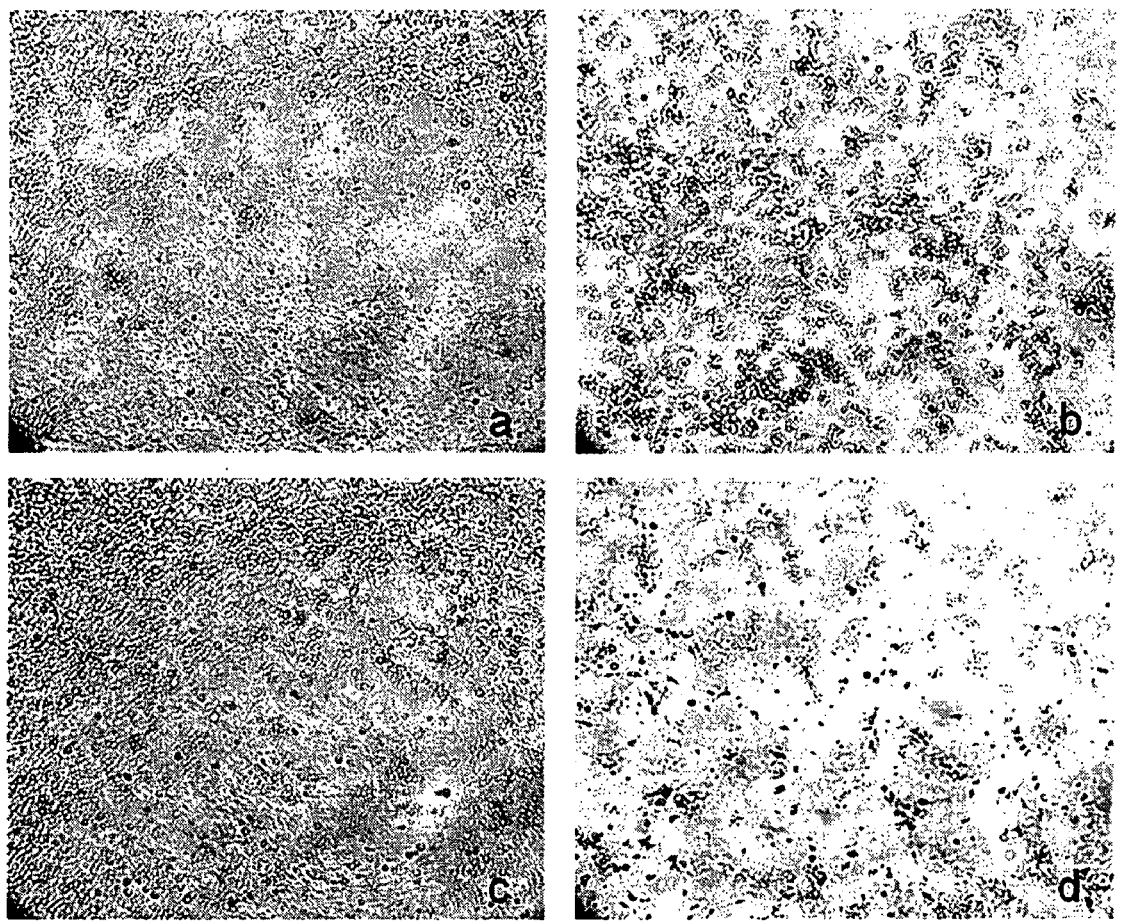

FIG. 3. Cytotoxicity assay of *C. perfringens* EHE-NE18 culture supernatant on LMH cells. a. TPG culture media (neat); b. *C. perfringens* EHE-NE18 culture supernatant (1:16 dilution); c. *C. perfringens* JIR325 (Strain 13—non necrotic enteritis strain) culture supernatant (1:2 dilution); *C. perfringens* NE18-M1 (plc mutant) culture supernatant (1:16 dilution).

Figure 4:
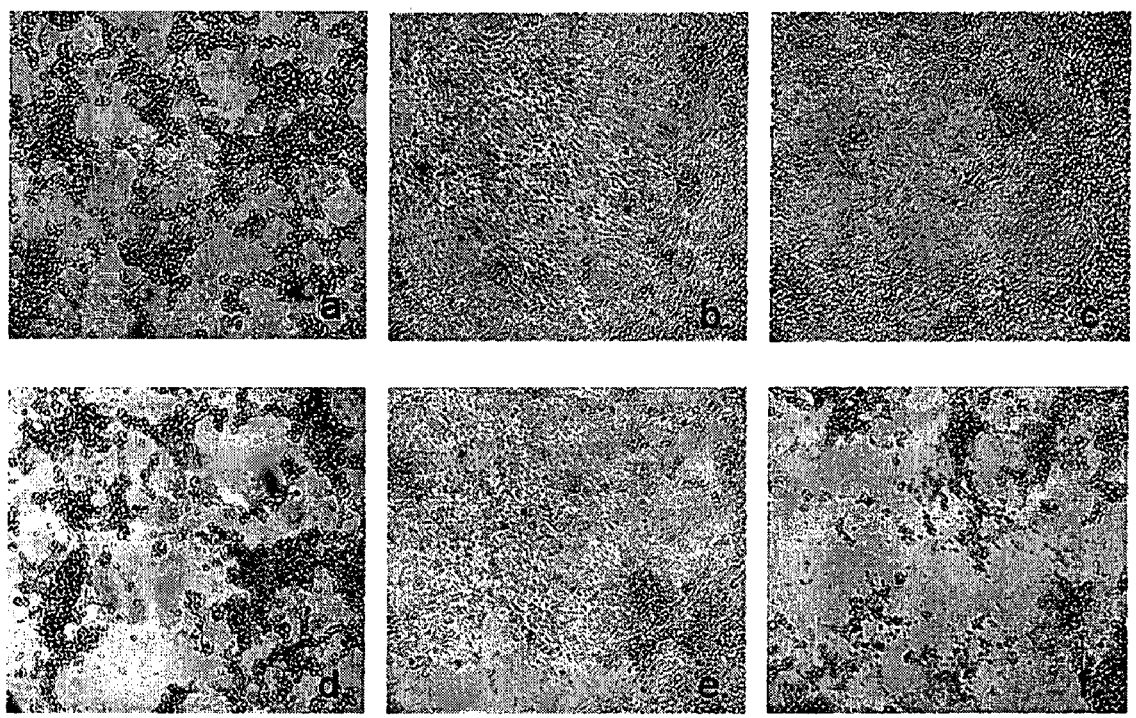

FIG. 4. Cytotoxicity assay of netB negative derivatives of EHE-NE18 culture supernatant on LMH cells. a. EHE-NE18 culture supernatant (1:16 dilution); b. NE18-Deleted netB1 culture supernatant (1:2 dilution); c. NE18-Deleted netB1+pJIR1457 (shuttle plasmid) culture supernatant (1:2 dilution); d. NE18-Deleted netB1+pALK20 (netB complementation plasmid) culture supernatant (1:16 dilution); e. TPG culture media (neat); f. Column purified recombinant NetB (1:8 dilution).

Figure 5:
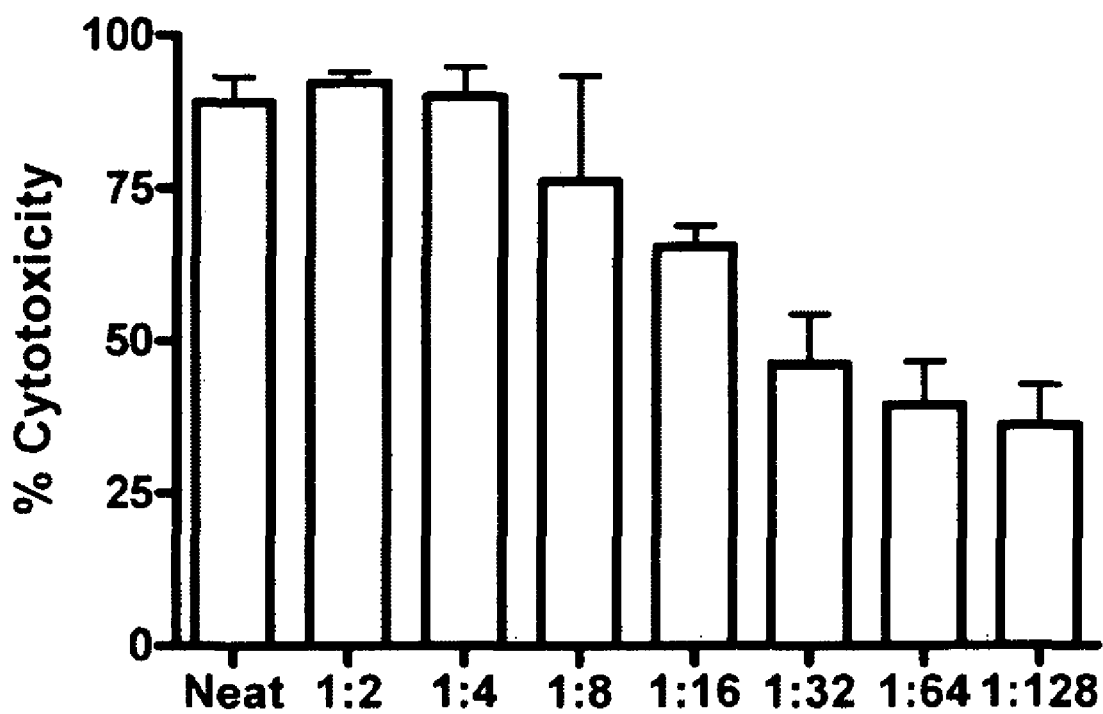

FIG. 5. Lactate dehydrogenase cytotoxicity assay of LMH cells treated with NetB. LDH released in the supernatant was measured as an indicator of cytolysis with a Cyto-Tox (Promega) kit and given as a percentage cytotoxicity. Each dilution was done in triplicate and SEM calculated for each dilution.

Figure 6:
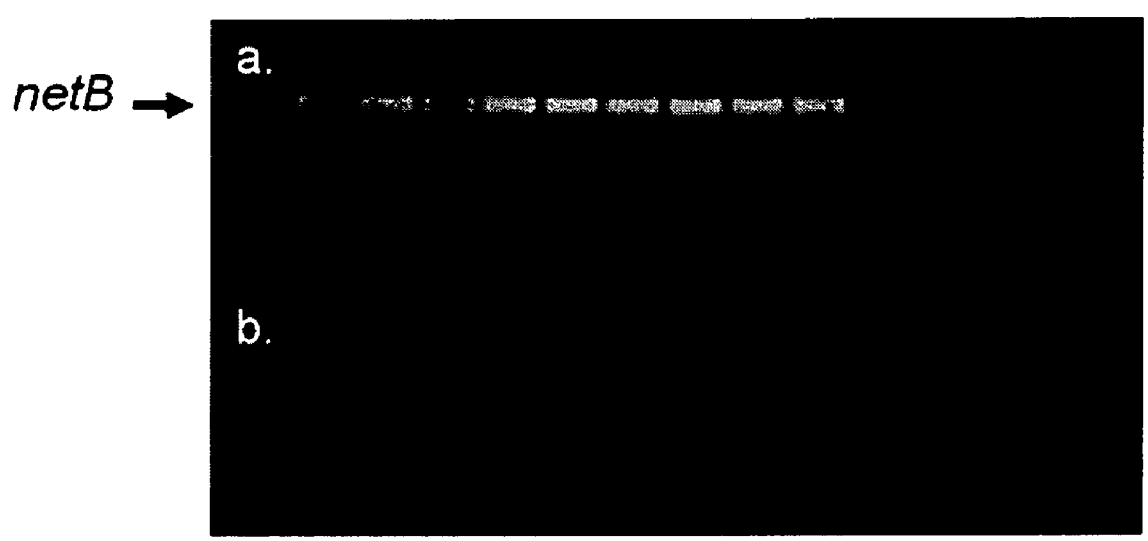

FIG. 6. PCR screening of NE and non-NE *C. perfringens* strains for the presence of netB. a. NE strains; b. Non-NE strains.

Figure 7:
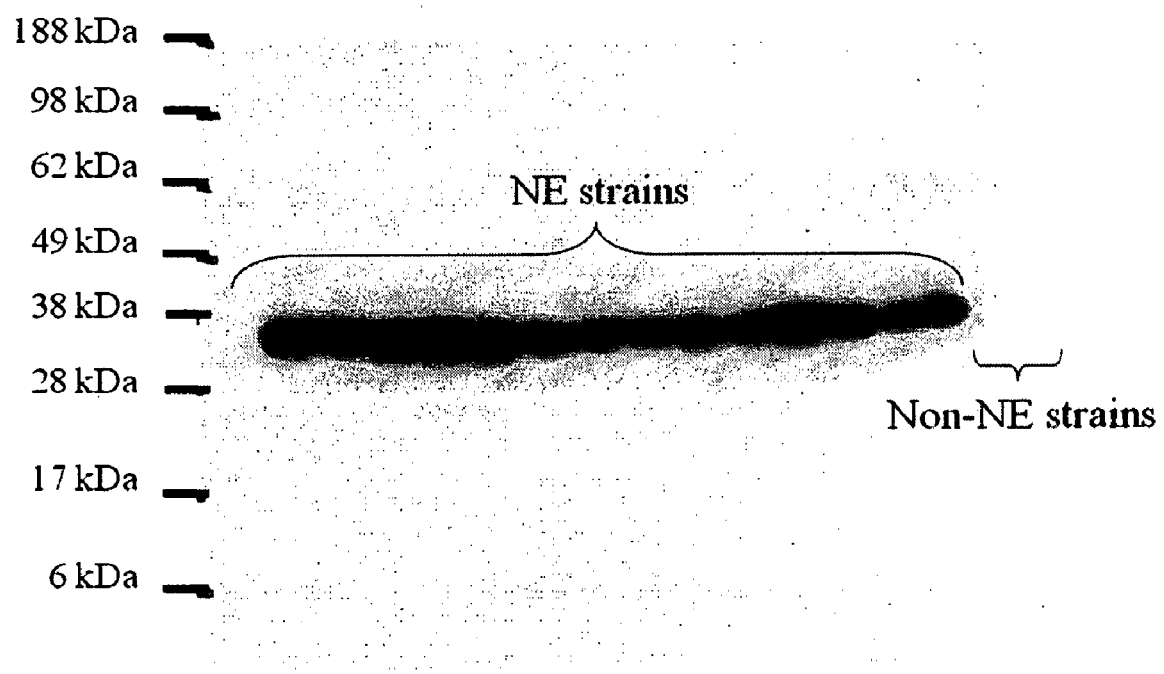

FIG. 7. Western blot survey for presence of protein in a variety of *C. perfringens* strains (NE and non-NE). Western blot analysis of NE strains and non-NE strains of *C. perfringens* screening for NetB expression. *C. perfringens* strains were grown in TPG media until they reached an OD600 nm of 0.6 and culture supernatants separated by SDS-PAGE. The separated proteins were transferred to PDVF membrane and probed with rNetB antiserum from rabbits. Brackets indicate NE and non-NE *C. perfringens* strains.

Figure 8:
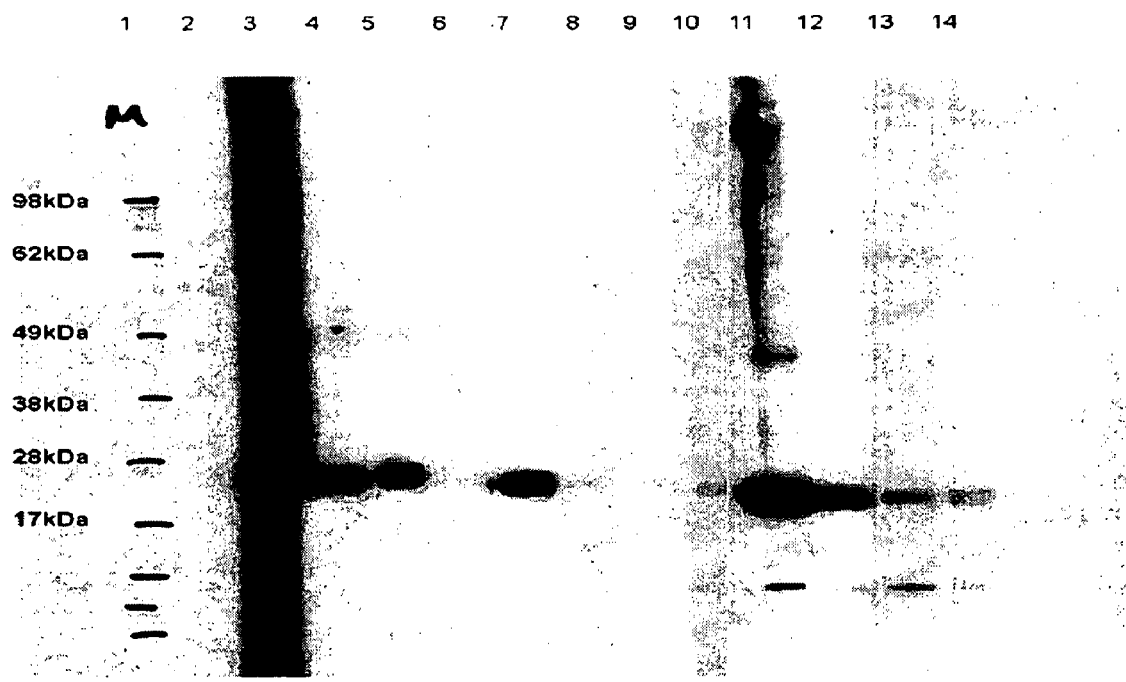

FIG. 8. Western blot analysis of sera from chickens vaccinated with NetB. Lane 1: Molecular weight marker (Invitrogen SeeBlue® Plus2 pre-stained standard); Lanes 2-14: serum from vaccinated birds #1-#13.

KEY TO THE SEQUENCE LISTING

SEQ ID NO:1—Nucleotide sequence encoding *Clostridium perfringens* NetB toxin.

SEQ ID NO:2—Mature amino acid sequence of *Clostridium perfringens* NetB toxin.

SEQ ID NO:3—Amino acid sequence of *Clostridium perfringens* NetB toxin including signal peptide sequence.

SEQ ID NO:4—Amino acid sequence of *Clostridium perfringens* beta-toxin.

SEQ ID Nos:5 to 10—Oligonucleotide primers.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in microbiology, cell culture, molecular genetics, immunology, immunohistochemistry, protein chemistry, and biochemistry).

Unless otherwise indicated, the recombinant protein, cell culture, microbiological and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present), and are incorporated herein by reference.

As used herein, the term "subject" refers to an animal, e.g., a bird or mammal. In a preferred embodiment, the subject is avian, for example a chicken. In another embodiment, the subject is a human. Other preferred embodiments include companion animals such as cats and dogs, as well as livestock animals such as horses, cattle, sheep and goats.

The term "avian" as used herein refers to any species, subspecies or race of organism of the taxonomic class Ayes, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Australorp, Cornish, Minorca, Amrox, California Gray, Italian Partidge-colored), as well as strains of turkeys, pheasants, quails, duck, ostriches and other poultry commonly bred in commercial quantities.

As used herein "toxin activity" refers to the ability of a polypeptide or peptide (e.g. NetB toxin) to kill, or cause a cytopathic effect in, animal cells. In some instances it may be desirable for a polypeptide to have reduced toxin activity compared to NetB toxin. Reduction of toxin activity is preferably at least 50, 60, 70, 80, 90, 95 or 99%. Reduction in toxin activity may be measured, for example, as a decrease in cytopathic effect.

The terms "cytopathic effect" or "CPE" as used herein describe changes in cellular structure as a result of the activity of a cellular toxin (i.e., a pathologic effect). Common cytopathic effects include cell destruction, cell rounding, syncytia (i.e., fused giant cells) formation, vacuole formation, and formation of inclusion bodies. CPE results from actions of a toxin on cells that negatively affect the ability of the cells to perform their required functions to remain viable. In in vitro cell culture systems, CPE is evident when cells, as part of a confluent monolayer, show regions of non-confluence after contact with a sample that contains a toxin. Cytopathic effects are readily discernable and distinguishable by those skilled in the art.

As used herein the term "toxoid" refers to any at least partially inactivated toxin but is not meant to limit in any way the particular means of inactivating a toxin to produce a toxoid. Such inactivating technologies include: (i) chemical methods that modify the intact toxin, e.g. formaldehyde or glutaraldehyde treatment; (ii) physical methods such as heating, (iii) enzymatic methods that alter the toxin, such as a protease that cleaves the toxin into fragments; (iv) recombinant methods, such as genetic engineering of the toxin gene to remove or alter enzymatic regions of the toxin, but retaining one or more antigenic epitopes.

The term "wild-type" as used herein in relation to bacteria refers to naturally occurring bacteria which produce a polypeptide comprising an amino acid sequence at least 40% identical, more preferably at least 90% identical to SEQ ID NO:2 or SEQ ID NO:3 which has toxin activity.

As used herein the terms "treating", "treat" or "treatment" include administering a therapeutically effective amount of a polypeptide, polynucleotide, vector, host cell, composition, vaccine and/or attenuated bacterium of the invention sufficient to reduce or eliminate at least one symptom of disease caused by infection with a bacterium expressing a polypeptide having toxin activity.

The term "preventing" refers to protecting a subject that may be exposed to a bacteria from developing at least one symptom resulting from infection and/or colonization by the bacteria, or reducing the severity of a symptom of infection and/or colonization in a subject exposed to the bacteria.

Polypeptides/Peptides

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, biologically active fragments, modifications, analogous and/or derivatives of the polypeptides described herein.

By "substantially purified polypeptide" or "isolated polypeptide" we mean a polypeptide that has generally been separated from the lipids, nucleic acids, other peptides, and other contaminating molecules with which it is associated in its native state. Preferably, the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. More preferably, the two sequences are aligned over their entire length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 40%, more preferably at least 45%, more preferably at least 50%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) polypeptides can be prepared using any suitable technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include toxin encoding genes related to those of the present invention, such as those from bacteria other than *Clostridium perfringens*. Products derived from mutated/altered DNA can readily be screened using techniques described herein to determine if they possess toxin activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

| Exemplary substitutions. | |
|---|---|
| Original Residue | Exemplary Substitutions |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Also included within the scope of the invention are biologically active fragments of the polypeptides of the present invention. As used herein a "biologically active fragment" is a portion of a polypeptide of the invention which maintains a defined activity of the full-length polypeptide. Biologically active fragments can be any size as long as they maintain the defined activity. Preferably, the biologically active fragment maintains at least 10% of the activity of the full length protein. As would be known to the skilled addressee, techniques for identifying a biologically active fragment of a polypeptide are known in the art. For example, a fragment of the polypeptide of the invention may be tested in a suitable assay to determine whether the fragment has toxin activity, for example by determining whether the fragment is able to induce a cytopathic effect in a cell. In one embodiment, the biologically active fragment is at least 100 amino acids in length, more preferably at least 110 amino acids in length, more preferably at least 120 amino acids in length, more preferably at least 130 amino acids in length, more preferably at least 140 amino acids in length, more preferably at least 150 amino acids in length, more preferably at least 175 amino acids in length, or more preferably 200 or more amino acids in length.

The terms "antigen" and "antigenic" are well understood in the art and refer to the portion of a macromolecule which is specifically recognized by a component of the immune system, e.g., an antibody or a T-cell antigen receptor. The term "antigen" refers to a peptide, a polypeptide, or other macromolecule to which an immune response can be induced in a host. Thus the invention includes an antigenic fragment of a polypeptide of the invention. Preferably, the antigenic fragment is capable of raising an immune response against a bacterial pathogen, for example a bacterium from the genus *Clostridium* including, but not limited to, *Clostridium perfringens*. In one embodiment, the antigen is an epitope of the polypeptide of the invention. In one embodiment, the antigenic fragment is 6 amino acids in length, more preferably 7 amino acids in length, more preferably 8 amino acids in length, more preferably 9 amino acids in length, more preferably at least 10 amino acids in length. Alternatively the antigenic fragment is at least 20, 30, 40, 50, 60, 70, 80, 90, 100 or more amino acids in length. In an embodiment, the antigen when administered to a subject is able to elicit an immune response against a polypeptide comprising an amino acid sequence as provided in SEQ ID NO:2 and/or SEQ ID NO:3.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a host cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Antibodies

The term "antibody" as used in this invention includes polyclonal antibodies, monoclonal antibodies, bispecific antibodies, diabodies, triabodies, heteroconjugate antibodies, chimeric antibodies including intact molecules as well as fragments thereof, such as Fab, F(ab')2, and Fv which are capable of binding the epitopic determinant, and other antibody-like molecules.

Antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

(6) Single domain antibody, typically a variable heavy domain devoid of a light chain.

Polyclonal Antibodies

An antibody of the present invention may be a polyclonal antibody. Methods of preparing polyclonal antibodies are known to the skilled artisan. Polyclonal antibodies can be raised in a mammal or avian, for example, by one or more injections of the cells expressing the polypeptide and, if desired, an adjuvant. Typically, the cells and/or adjuvant will be injected in the mammal or avian by multiple subcutaneous or intraperitoneal injections. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal Antibodies

The antibodies produced by the method of the invention may, alternatively, be monoclonal antibodies. Monoclonal antibodies may be prepared using hybridoma methods, such as those described by Kohler and Milstein, (1975). In a hybridoma method, a mouse, hamster, or other appropriate host animal, is typically immunized with the cells expressing the polypeptide of the first species derived from the transgenic mammal to elicit lymphocytes that produce or are capable of producing antibodies that will specifically bind to the polypeptide of the first species.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, 1985; Brodeur et al., Monoclonal Antibody Production Techniques and Applications, Marcel Dekker, Inc., New York, 1987 pp. 51-63).

The culture medium in which the hybridoma cells are cultured can then be assayed for the presence of monoclonal antibodies directed against the polypeptide of the first species. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, (1980).

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The antibodies may also be affinity matured using known selection and/or mutagenesis methods as are known in the art. Preferred affinity matured antibodies have an affinity which is five times, more preferably 10 times, even more preferably 20 or 30 times greater than the starting antibody from which the matured antibody is prepared.

Bispecific Antibodies

Bispecific antibodies are monoclonal antibodies that have binding specificities for at least two different antigens. For example, one of the binding specificities may be for a polypeptide of the invention, the other one may be for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, 1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker (1991).

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Various technique for making and isolating bispecific antibody fragments directly from recombinant cell culture have also been described.

Hollinger et al. (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported by Gruber et al. (1994).

Antibodies with more than two valencies are contemplated. For example, trispecific antibodies can be prepared. Tutt et al. (1991).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Polynucleotides

By "isolated polynucleotide" we mean a polynucleotide which has generally been separated from the polynucleotide sequences with which it is associated or linked in its native state. Preferably, the isolated polynucleotide is at least 60% free, more preferably at least 75% free, and more preferably at least 90% free from other components with which it is naturally associated. Furthermore, the term "polynucleotide" is used interchangeably herein with the terms "nucleic acid molecule", "gene" and "mRNA".

The term "recombinant" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. A recombinant polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

"Polynucleotide" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein.

The % identity of a polynucleotide is determined by GAP (Needleman and Wunsch, 1970) analysis (GCG program) with a gap creation penalty=5, and a gap extension penalty=0.3. The query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. Even more preferably, the query sequence is at least 300 nucleotides in length and the GAP analysis aligns the two sequences over a region of at least 300 nucleotides. More preferably, the two sequences are aligned over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 40%, more preferably at least 45%, more preferably at least 50%, more preferably at least 55%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis or DNA shuffling on the nucleic acid as described above). It is thus apparent that polynucleotides of the invention can be either naturally occurring or recombinant.

Polynucleotides of the invention include those which hybridize under stringent conditions to a polynucleotide comprising a sequence of nucleotides which is at least 40% identical, more preferably at least 90% identical, to SEQ ID NO:1. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA).

Vectors and Host Cells

One embodiment of the present invention includes a recombinant vector, which comprises at least one isolated polynucleotide molecule of the present invention, inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

"Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, an expression vector is a DNA or RNA vector that is capable of transforming a host cell and of effecting expression of a specified polynucleotide molecule.

Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Recombinant molecules may also include intervening and/or untranslated sequences surrounding and/or within the nucleic acid sequences of nucleic acid molecules of the present invention.

Another embodiment of the present invention includes a host cell comprising one or more recombinant molecules of the present invention. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide molecule of the present invention. Host cells of the present invention can be any cell capable of producing at least one protein of the present invention, and include animal, plant, bacterial, fungal (including yeast), parasite, and arthropod cells. Preferably, the host cell is a bacterial cell. In one preferred embodiment, the host cell is an *E. coli* strain having the serotype H antigen, H10. Examples of suitable *E. coli* strains include CCEC22, CCEC31, and CCEC59 as described in WO 2007/025333.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Detection of Polynucleotides

Any suitable technique that allows for the detection of a polynucleotide of the invention may be used, including those that allow quantitative assessment of the level of expression of the polynucleotide in a tissue and/or cell. For example, the presence or levels of a transcribed gene can be determined by Northern blotting, and/or amplification of the polynucleotide, such as by PCR. Comparison may be made by reference to a standard control. For example, levels of a transcribed gene can be determined by Northern blotting, and/or RT-PCR. With the advent of quantitative (real-time) PCR, quantitative analysis of gene expression can be achieved by using appropriate primers for the gene of interest. The nucleic acid may be labelled and hybridised on a gene array, in which case the gene concentration will be directly proportional to the intensity of the radioactive or fluorescent signal generated in the array.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from biological samples. However, it will generally be easier if PCR is performed on genomic DNA.

A primer is an oligonucleotide, usually of about 20 nucleotides long, with a minimum of about 15 nucleotides, that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the induction of restriction enzyme or catalytic nucleic acid recognition/cleavage sites in specific target sequences. Primers may also contain additional sequences and/or modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

The skilled person will understand that there are numerous alternative techniques for amplifying a polynucleotide of the present invention. Examples of other amplification techniques include reverse transcription polymerase chain reaction (RT-PCR), ligase chain reaction ("LCR"), and also include isothermal amplification techniques such as strand displacement amplification (SDA), loop-mediated isothermal amplification of DNA (LAMP).

Alternatively, polynucleotides of the present invention may be detected in a sample using suitable hybridization techniques, for example Southern blot hybridization with suitably labelled probes. A "probe" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. Probes specific for the polynucleotides described herein, or portions thereof, may vary in length by any integer from at least 8 nucleotides to over 500 nucleotides, including any value in between, depending on the purpose for which, and conditions under which, the probe is used. For example, a probe may be at least 8, 10, 15, 20, or 25 nucleotides in length, or may be at least 30, 40, 50, or 60 nucleotides in length, or may be over 100, 200, 500, or 1000 nucleotides in length. Probes specific for the polynucleotides described herein are generally at least 40%, 50%, 55% or 60%, or at least 65%, 75%, 80%, 85%, 90%, or 95%, or as much as 96%, 97%, 98%, or 99% identical to the nucleic acid sequences described herein using for example the Align program (Myers and Miller, 1989).

The term "hybridization" as used herein refers to the association of two nucleic acid molecules with one another by hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al., Molecular Cloning; A Laboratory Manual, Second Edition (1989)). In accordance with these principles, the inhibition of hybridization of a complementary molecule to a target molecule may be examined using a hybridization assay; a substantially homologous molecule possessing a greater degree of homology will then compete for and inhibit the binding of a completely homologous molecule to the target molecule under various conditions of stringency, as taught in Wahl et al., (1987).

As used herein in relation to hybridisation, "stringent conditions" are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2× SSC and 0.1% SDS.

Attenuated Bacteria

Methods of attenuating the virulence of bacterial pathogens are known in the art. Typically, mutations are introduced into a bacterial genome to prevent or reduce expression of toxins or other virulence genes to delete or inactivate the gene. In some instances they knock-out the function of the gene completely. This may be achieved either by abolishing synthesis of any polypeptide at all from the gene or by making a mutation that results in synthesis of non-functional polypeptide. In order to abolish synthesis of polypeptide, either the entire gene or its 5'-end may be deleted. A deletion or insertion within the coding sequence of a gene may be used to create a gene that synthesises only non-functional polypeptide (e.g. polypeptide that contains only the N-terminal sequence of the wild-type protein). In the case of a toxin gene, the mutation may render the gene product non-toxic.

A "mutation" includes any alteration in the DNA sequence, i.e. genome, of an organism, when compared with the parental strain. The alterations may arise by exposing the organism to a mutagenic stimulus, such as a mutagenic chemical, energy, radiation, recombinant techniques, mating, or any other technique used to alter DNA. A mutation may include an alteration in any of the nucleotide sequences described herein, or may include an alteration in a nucleotide sequence encoding any of the polypeptides described herein.

A mutation may "attenuate virulence" if, as a result of the mutation, the level of virulence of the mutant cell is decreased by at least 10%, 20%, 30%, 40%, 50%, 60%, 70%, 80%, 90%, or 100%, when compared with the parental strain. Decrease in virulence may also be measured by a decrease of at least 10%, 20%, 30%, 40%, 50%, 60%, 70%, 80%, 90%, or 100% in the expression and/or toxin activity of a polypeptide, for example, a polypeptide comprising an amino acid sequence substantially identical to the sequence of SEQ ID NO:2 or SEQ ID NO:3, or a fragment or variant thereof, in the mutant strain when compared with the parental strain.

The skilled person will appreciate that an attenuated bacterial pathogen of the present invention may be suitable for the delivery of one or more biologically active polypeptides to a subject. Examples of biologically active polypeptides suitable for delivery by an attenuated bacteria of the invention include ones which are capable of functioning locally or systemically, e.g., is a polypeptide capable of exerting endocrine activities affecting local or whole-body metabolism.

In one embodiment, the biologically active polypeptide may be a heterologous polypeptide. The term "heterologous polypeptide" is well understood in the art and refers to a polypeptide which is not endogenous to a cell. The nucleic acid molecule encoding the polypeptide of interest may originate from any organism capable of producing the polypeptide of interest or may be a completely synthetic gene. The nucleic acid molecule encoding the polypeptide can be added to the cell by, for example, infection, transfection, microinjection, electroporation, microprojection, or the like.

By way of example, the biologically active polypeptide may be one which is capable of regulating the immunohemopoietic system. Alternatively, the biologically active polypeptide may be one which is capable of affecting the viability, growth and differentiation of a variety of normal or neoplastic cells in the body. Alternatively, the biologically active polypeptide may be one which is capable of affecting the immune regulation or induction of acute phase inflammatory responses to injury and infection. Alternatively, the biologically active polypeptide may be one which is capable of enhancing or inducing resistance to infection of cells and tissues mediated by chemokines acting on their target cell receptors, or the proliferation of epithelial cells or the promotion of wound healing.

Specific examples of such polypeptides include insulin, growth hormone, prolactin, calcitonin, luteinizing hormone, parathyroid hormone, somatostatin, thyroid-stimulating hormone, vasoactive intestinal polypeptide, a structural group 1 cytokine such as IL-1β, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-23, IL-24, IL-25, IL-26, IL-32, cMGF, LT, GM-CSF, M-CSF, SCF, IFN-γ, IFN-λ, EPO, G-CSF, LIF, OSM, CNTF, GH, PRL or IFNα/β, a structural group 2 cytokine such as the TNF family of cytokines, e.g., TNFα, TNFβ, CD40, CD27 or FAS ligands, the IL-1 family of cytokines, the fibroblast growth factor family, the platelet-derived growth factors, transforming growth factor β and nerve growth factors, a structural group 3 cytokine, e.g., the epidermal growth factor family of cytokines, the chemokines, the insulin-related cytokines, a structural group 4 cytokine such as the heregulins or neuregulins, e.g., EGF.

Alternatively, the biologically active polypeptide can be a receptor or antagonist for biologically active polypeptides as defined above.

In another embodiment of the invention, the biologically active polypeptide is an antibody, preferably a recombinant antibody.

Alternatively, the biologically active polypeptide can be an antimicrobial peptide or a synthetic variant thereof. Antimicrobial peptides include cecropins, magainins, and defensins. Cecropins were the first well-characterized family of structurally related antimicrobial peptides and are found in a wide distribution of insects (Boman, 2003). In vertebrates, the magainin family of antimicrobial peptides have been isolated from the glands of the skin and gastrointestinal tract of *Xenopus laevis*, and are thought to form the basis for the defense system of the amphibian mucosal surfaces against infection. (Soravia et al., 1988).

Defensins are antimicrobial peptides found in phagocytic cells isolated from several mammalian species including man and may be characterized by eight invariant residues within the sequence. (Gabay et al., 1989). The mechanism of antimicrobial activity of peptides such as the defensins is via a selective membrane disruption leading to a characteristic broad spectrum of antibiotic activity. (Boman, 1995). The antimicrobial spectrum of defensins includes gram positive and gram negative bacteria, mycobacteria, many fungi, and some enveloped-viruses.

Antimicrobial peptides of bacterial origin are known as microcins, colicins and bacteriocins (Jack et al., 1995; Ingham et al., 2003). It is known that the sequence, structure and mechanisms of activity of bacteriocins are diverse. The most abundant and thoroughly studied bacteriocins include class I (lantibiotics) and class II (small heat-stable non-lanthionine-containing peptides) bacteriocins (Ennahar et al., 2000). The class II bacteriocins form an important subgroup because of their activities and potential applications. The class IIa bacteriocins include Piscicolin 126, leucocin A and enterocin P amongst others. The class IIa bacteriocins have the common N-terminal motif: YGNGVXaaCXaa(K/N)XaaXaaCXaaV (N/D)(W/K/R)Xaa-(G/A/S)(A/N), where residues with higher variability are represented by Xaa (Bhugaloo-Vial, et al., 1996). In an example demonstrating the antimicrobial properties of bacteriocins, Piscicolin 126, which when injected into mice, was shown to display in vivo antimicrobial activity and significantly reduced the listerial load in the liver and the spleen (Ingham et al., 2003).

Alternatively, the biologically active polypeptide can be an enzyme. The enzyme can be any enzyme having a desired activity. For example, it may be desirable to deliver an enzyme that plays a role in improving the digestibility of food or the removal of anti-nutritive compounds. For example, polysaccharide-degrading and fibrolytic enzymes such as xylanases (Liu et al., 2005), glucanases (Cho et al., 2000), cellulases (Liu et al., 2005), amylases, levansucrases, and inulosucrases may be delivered to increase the digestibility of food. Proteinases, peptidases, and lipases may also be delivered in order to increase the nutritive value of ingested foods. Phytases (Vohra and Satyanarayana, 2003; Nahashon et al., 1994) and acid phosphatases (Palacios et al., 2005) may be delivered to reduce the anti-nutritive effects of phytate that is found in plant seeds.

In another embodiment, the attenuated bacterial pathogen of the invention may express an antigen. If the antigen is from, for example, a bacterial, fungal, parasitic or viral disease agent, the attenuated bacterial strain can be used to vaccinate a subject against diseases caused by such agents. For example, the attenuated bacterial strain could be used to deliver an antigen from an avian pathogenic micro-organism. Such micro-organisms include but are not limited to species of *Corynebacteria, Mycoplasma, Listeria, Borrelia, Chlamydia, Clostridia, Coxiella, Eysipelothrix, Flavobacteria, Staphylococcus, Escherichia, Salmonella, Campylobacter*, and *Streptococcus*. Examples of fungal and parasitic avian pathogens known to infect poultry are species of *Amoebotaenia, Aproctella, Ascaridia, Aspergillus, Candida, Capillaria, Cryptosporidium, Cyathostroma, Dispharynx, Eimeria, Fimbriaria, Gongylonemia, Heterakis, Histomonas, Oxyspirura, Plasmodium, Raillietina, Strongyloides, Subulura, Syngamus, Tetrameres*, and *Trichostrongylus*. Viruses known to infect poultry include adenoviruses (e.g., hemorrhagic enteritis virus), astroviruses, coronaviruses (e.g., Infectious bronchitis virus), paramyxoviruses (e.g., Newcastle disease virus), picornaviruses (e.g., avian encephalomyelitis virus), pox viruses, retroviruses (e.g., avian leukosis/sarcoma viruses), reoviruses, and rotaviruses. Specific examples include Avian Influenza, Marek's Disease Virus and Chicken Anaemia Virus. Preferred gene products for use as antigens are polypeptides and peptides, including glycoproteins and lipoproteins. Antigen-encoding genes from these prokaryotic and eukaryotic organisms can be cloned and expressed in the attenuated bacteria using standard techniques.

Compositions and Administration

An "immunogenic composition" refers to a composition that comprises materials that elicit a desired immune response and includes a "vaccine". The term "vaccine" covers any composition that induces an at least partially protective immune response against the targeted pathogen or which efficaciously protects against the pathogen; for instance, after administration or injection into the animal (e.g., avian such as chicken or porcine such as pig), elicits an at least partially protective immune response against the targeted pathogen or provides efficacious protection against the pathogen (e.g., *C. perfringens*). A subunit of a pathogen, e.g. an antigen or immunogen or epitope isolated from the pathogen, and a subunit composition comprises or consists essentially of one or more antigens, immunogens or epitopes isolated from the pathogen. By inducing an "at least partially protective" immune response it is meant that a vaccine reduces infection and/or colonization by a bacteria expressing a polypeptide of the invention or reduces at least one symptom caused by infection with a bacteria expressing a polypeptide of the invention.

An immunogenic composition may select, activate or expand cells of the immune system including memory B and T cells to, for example, enable the elimination of infectious agents, such as bacterial pathogens expressing a polypeptide comprising the amino acid sequence of SEQ ID NO:2 and/or SEQ ID NO:3, or antigenic fragments thereof.

In some embodiments, an immunogenic composition includes a suitable carrier, such as an adjuvant, which is an agent that acts in a non-specific manner to increase the immune response to a specific antigen, or to a group of antigens, enabling the reduction of the quantity of antigen in any given dose, or the reduction of the frequency of dosage required to generate the desired immune response. A desired immune response may include, for example, full or partial protection against shedding of (presence in faeces of an infected animal, e.g., mammal or avian) or colonization (presence in the intestine of an infected animal, e.g., mammal or avian) by a bacterial pathogen. For example, a desired immune response may include any value from between 10% to 100%, e.g., 50%, 60%, 70%, 80%, 90%, 100%, protection against shedding of or colonization by a bacterial pathogen in a vaccinated animal when compared to a non-vaccinated animal.

Adjuvants are useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention further comprise an adjuvant. Examples of chemical compounds that can be used as adjuvants include, but are not limited to aluminum compounds (e.g., aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12) and CARBOPOL®.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens.

Generally, an adjuvant is administered at the same time as an antigen of the present invention. However, adjuvants can also, or alternatively be administered within a two-week period prior to the vaccination, and/or for a period of time after vaccination, i.e., so long as the antigen, e.g., a polypeptide comprising an amino acid sequence as provided in SEQ ID NO:2 or SEQ ID NO:3 or an antigenic fragment thereof, persists in the tissues.

Immunogenic compositions according to the invention may include the polypeptides and nucleic acid molecules described herein, or immunogenic fragments thereof, and may be administered using any form of administration known in the art or described herein. In some embodiments of the invention, the immunogenic composition or vaccine may include a live bacterial pathogen, a killed bacterial pathogen, or components thereof. Live bacterial pathogens, which may be administered in the form of an oral vaccine, may be attenuated so as to reduce the virulence of the bacterial pathogen, but not its induction of an immune response. A live vaccine may be capable of colonizing the intestines of the inoculated animal, e.g., avian.

In some embodiments, the polypeptides and nucleic acid molecules described herein, or antigenic fragments thereof, or the mutated bacteria (e.g., attenuated bacteria) described herein may be administered to poultry, e.g., chicken, ducks, turkeys, etc., so as to elicit an immune response e.g., raise antibodies, in the poultry. Eggs, or products thereof, obtained from such poultry, that exhibit an immune response against the polypeptides and nucleic acid molecules described herein, or immunogenic fragments thereof, may be administered to an animal, e.g., humans, cattle, goats, sheep, etc., to elicit an immune response to the polypeptides and nucleic acid molecules described herein, or immunogenic fragments thereof, in the animal. Methods of raising antibodies in poultry, and administering such antibodies, are described in for example, U.S. Pat. No. 5,750,113 and U.S. Pat. No. 6,730,822.

The immunogenic compositions and vaccines according to the invention may be further supplemented by the addition of other recombinant or purified antigens which may result in the production of antibodies of a variety of specificities when administered to an animal subject. Not all of these antibodies need to be protective against a disease. In a particular embodiment of this type, such antigens are also from *C. perfringens*. Thus, a vaccine of the present invention may contain various other active or inactivated pathogenic factors, along with the polypeptide of the invention. Therefore, in accordance with the present invention, the polypeptide of the invention can be combined with other clostridial and non-clostridial cells, toxoids, and extracts.

The additional antigens may comprise a viral antigen and/or a bacterial antigen and/or a parasite antigen. For example, the antigen may be derived from a micro-organism including, but not limited to, species of *Corynebacteria, Mycoplasma, Listeria, Borrelia, Chlamydia, Clostridia, Coxiella, Eysipelothrix, Flavobacteria, Staphylococcus, Escherichia, Salmonella, Campylobacter*, and *Streptococcus*. Examples of fungal and parasitic avian pathogens known to infect poultry are species of *Amoebotaenia, Aproctella, Ascaridia, Aspergillus, Candida, Capillaria, Cryptosporidium, Cyathostroma, Dispharynx, Eimeria, Fimbriaria, Gongylonemia, Heterakis, Histomonas, Oxyspirura, Plasmodium, Raillietina, Strongyloides, Subulura, Syngamus, Tetrameres*, and *Trichostrongylus*. Viruses known to infect poultry include adenoviruses (e.g., hemorrhagic enteritis virus), astroviruses, coronaviruses (e.g., Infectious bronchitis virus), paramyxoviruses (e.g., Newcastle disease virus), picornaviruses (e.g., avian encephalomyelitis virus), pox viruses, retroviruses (e.g., avian leukosis/sarcoma viruses), reoviruses, and rotaviruses.

A multivalent vaccine of the present invention can also comprise one or more of the following antigens: *C. perfringens* beta toxin, *C. perfringens* beta 2 toxin, *C. perfringens* enterotoxin, *C. perfringens* epsilon toxin, *C. perfringens* iota toxin, *C. perfringens* kappa toxin, *C. perfringens* lambda toxin, *C. perfringens* theta toxin, *C. sordellii* hemorrhagic toxin, *C. sordellii* lethal toxin, *C. difficile* A toxin, *C. difficile* B toxin, *C. septicum* alpha toxin, *C. novyi* alpha toxin, and *C. novyi* beta toxin.

The immunogenic compositions and vaccines of the present invention may be administered as a liquid, emulsion, dried powder and/or in a mist through any parenteral route, intravenously, intraperitoneally, intradermally, by scarification, subcutaneously, intramuscularly, or inoculated by a mucosal route, e.g., orally, intranasally, as an aerosol, by eye drop, by in ovo administration, or implanted as a freeze dried powder.

Administration of the polypeptide and nucleic acid molecules described herein, or immunogenic fragments thereof, the mutated bacteria (e.g., attenuated bacteria) and/or the immunogenic compositions described herein may be conveniently achieved by injection into the egg of an avian, (e.g., poultry) and generally injection into the air sac. Notwithstanding that the air sac is the preferred route of in ovo administration, other regions such as the yolk sac or chorion allantoic fluid may also be inoculated by injection. The hatchability rate might decrease slightly when the air sac is not the target for the administration although not necessarily at commercially unacceptable levels. The mechanism of injection is not critical to the practice of the present invention, although it is preferred that the needle does not cause undue damage to the egg or to the tissues and organs of the developing embryo or the extra-embryonic membranes surrounding the embryo.

Generally, a hypodermic syringe fitted with an approximately 22 gauge needle is suitable. The method of the present invention is particularly well adapted for use with an automated injection system, such as those described in U.S. Pat. No. 4,903,635, U.S. Pat. No. 5,056,464, U.S. Pat. No. 5,136,979 and US 20060075973.

The present invention also provides methods of providing passive immunity to the progeny of a female animal (e.g., a pregnant female) comprising administering a vaccine of the present invention to the female animal (e.g., mother) prior to the birth of her progeny. "Passive immunity" refers to transfer of immunity from mother to progeny and can be accomplished inter alia through the ingestion of colostrums, as occurs in mammals, or the absorption of antibody into the bloodstream from the egg yolk, as occurs in poultry.

In one embodiment, the female is an avian and the vaccine is administered to the avian female prior to her laying of the eggs that comprise the progeny. In this manner her progeny are provided passive immunity. In one such embodiment, the avian is poultry. Preferably, the poultry is a chicken, turkey or duck.

The immunogenic compositions and vaccines of the present invention may comprise a pharmaceutically acceptable carrier. A pharmaceutically acceptable carrier includes a veterinarily acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like.

Generally, the ingredients of formulations of the invention are supplied either separately or mixed together in unit dosage form, for example, as a dry lyophilized powder or water free concentrate in a hermetically sealed container such as an ampoule or sachet indicating the quantity of active agent.

Also provided are compositions comprising a polypeptide of the invention, polynucleotide of the invention, vector of the invention and/or host cell of the invention. As would be appreciated by the skilled person, the compositions may comprise suitable carriers or excipients.

DNA Vaccines

DNA vaccination involves the direct in vivo introduction of DNA encoding an antigen into cells and/or tissues of a subject for expression of the antigen by the cells of the subject's tissue. Such vaccines are termed herein "DNA vaccines" or "nucleic acid-based vaccines." Examples of DNA vaccines are described in U.S. Pat. No. 5,939,400, U.S. Pat. No. 6,110,898, WO 95/20660 and WO 93/19183. The ability of directly injected DNA that encodes an antigen to elicit a protective immune response has been demonstrated in numerous experimental systems (see, for example, Conry et al., 1994; Cardoso et al., 1996; Montgomery et al., 1993; Yang et al., 1997).

A factor known to affect the immune response elicited by DNA immunization is the method of DNA delivery, for example, parenteral routes can yield low rates of gene transfer and produce considerable variability of gene expression (Montgomery et al., 1993). High-velocity inoculation of plasmids, using a gene-gun, enhanced the immune responses of mice (Fynan et al., 1993), presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

Vaccines Derived from Transgenic Plants

The term "plant" refers to whole plants, plant organs (e.g. leaves, stems roots, etc), seeds, plant cells and the like. Plants contemplated for use in the practice of the present invention include both monocotyledons and dicotyledons. Exemplary dicotyledons include corn, tomato, potato, bean, soybean, and the like. Typically the transgenic plant is routinely used as a feed source for farm animals, particularly chickens.

Transgenic plants, as defined in the context of the present invention include plants (as well as parts and cells of said plants) and their progeny which have been genetically modified using recombinant DNA techniques to cause or enhance production of at least one polypeptide of the present invention in the desired plant or plant organ.

Several techniques exist for introducing foreign genetic material into a plant cell, and for obtaining plants that stably maintain and express the introduced gene. Such techniques include acceleration of genetic material coated onto microparticles directly into cells (see, for example, U.S. Pat. No. 4,945,050 and U.S. Pat. No. 5,141,131). Plants may be transformed using Agrobacterium technology (see, for example, U.S. Pat. No. 5,177,010, U.S. Pat. No. 5,104,310, U.S. Pat. No. 5,004,863, U.S. Pat. No. 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques described herein.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of plant promoters include, but are not limited to ribulose-1,6-bisphosphate carboxylase small subunit, beta-conglycinin promoter, phaseolin promoter, ADH promoter, heat-shock promoters and tissue specific promoters. Promoters may also contain certain enhancer sequence elements that may improve the transcription efficiency. Typical enhancers include but are not limited to Adh-intron 1 and Adh-intron 6.

Constitutive promoters direct continuous gene expression in all cells types and at all times (e.g., actin, ubiquitin, CaMV 35S). Tissue specific promoters are responsible for gene expression in specific cell or tissue types, such as the leaves or seeds (e.g., zein, oleosin, napin, ACP, globulin and the like) and these promoters may also be used. Promoters may also be active during a certain stage of the plants' development as well as active in plant tissues and organs. Examples of such promoters include but are not limited to pollen-specific, embryo specific, corn silk specific, cotton fiber specific, root specific, seed endosperm specific promoters and the like.

Under certain circumstances it may be desirable to use an inducible promoter. An inducible promoter is responsible for expression of genes in response to a specific signal, such as: physical stimulus (heat shock genes); light (RUBP carboxylase); hormone (Em); metabolites; and stress. Other desirable transcription and translation elements that function in plants may be used.

In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the cauliflower mosaic virus (35S and 19S) and the like may be used.

A number of plant-derived edible vaccines are currently being developed for both animal and human pathogens (Hood and Jilka, 1999). Immune responses have also resulted from oral immunization with transgenic plants producing virus-like particles (VLPs), or chimeric plant viruses displaying antigenic epitopes (Modelska et al., 1998; Kapustra et al., 1999). It has been suggested that the particulate form of these VLPs or chimeric viruses may result in greater stability of the antigen in the stomach, effectively increasing the amount of antigen available for uptake in the gut (Modelska et al. 1998).

Feed

In one embodiment, a composition of the invention is a feed or feedstuff. For purposes of the present invention, "feed" or "feedstuffs" include any food or preparation for human or animal consumption (such as cattle, horses, goats and sheep) (including for enteral and/or parenteral consumption) which when taken into the body (a) serve to nourish or build up tissues or supply energy; and/or (b) maintain, restore or support adequate nutritional status or metabolic function.

The feeds include nutritional substances such as edible macronutrients, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of substances with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed starch. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feed compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feed compositions of the present invention can be of semi-purified or purified origin. By semi-purified or purified is meant a material which has been prepared by purification of a natural material or by de novo synthesis.

In an embodiment, the polypeptide of the invention is used in the production of the feed. For example, feed comprising the polypeptide of the invention can be used for vaccinating animals to provide at least partial protection from infection and/or colonization by a bacterial pathogen expressing a polypeptide with toxin activity, Preferably, the bacterial pathogen expresses a polypeptide comprising an amino acid sequence which is at least 40% identical to SEQ ID NO:2 and/or SEQ ID NO:3. In one embodiment, the bacterial pathogen is from the genus *Clostridium*, for example, the bacterial pathogen is *Clostridium perfringens*.

In another embodiment, the feed comprises a transgenic plant of the invention, and/or a part of said plant, and/or an extract of said plant.

Agonists and Antagonists—Assays and Molecules

The polypeptides of the invention may be employed in a screening process for compounds which activate (agonists) or inhibit (antagonists) the toxin activity of the polypeptide.

Examples of potential antagonists include antibodies, oligosaccharides and derivatives thereof. A potential antagonist includes a small molecule which binds to the polypeptide of the invention, making it inaccessible to a substrate of the polypeptide. Examples of small molecules include, but are not limited to, small peptides or peptide-like molecules. The small molecules may mimic the structure of a substrate of the polypeptide according to the invention.

The invention also comprehends high-throughput screening (HTS) assays to identify compounds that interact with or inhibit the biological activity (i.e., affect enzymatic activity) of a polypeptide having toxin activity. HTS assays permit screening of large numbers of compounds in an efficient manner. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the toxin polypeptide.

Antagonists of the polypeptide of the invention may be utilised to protect animals from disease by adding them to the animals feed or drink. Such treatment can reduce the load of active environmentally derived organisms that the animal is exposed to. Accordingly, the invention provides feed and/or drink comprising an antagonist of the polypeptide of the invention. The antagonist may be, for example, an antibody which binds a polypeptide of the invention. The present invention also provides the use of feed and/or drink comprising such antagonists to reduce infection and/or colonization of an animal with a bacteria which expresses a polypeptide of the invention.

EXAMPLES

Example 1

*Clostridium perfringens* NetB Toxin

Sequencing of the Gene Encoding NetB

10 μg of genomic DNA isolated from *Clostridium perfringens* strain EHE-NE18 was used to obtain sequence reads, contigs and sequence quality scores. An amino acid sequence was deduced from the nucleotide sequence. Prediction of a signal peptide was performed using the SignalP v 3.0 program (Bendtsen et al., 2004). Sequences homologous to the deduced amino acid sequence were searched using the gapped BLAST program (Altschul et al., 1997).

The nucleotide sequence of the gene encoding NetB is provided as SEQ ID NO:1 and the amino acid sequence of NetB including the signal sequence is provided as SEQ ID NO:3. The signal peptide sequence is cleaved from the mature secreted protein (SEQ ID NO:2). A BLAST search identified *C. perfringens* beta-toxin as sharing less than 39% identity with NetB (FIG. 1).

Purification of Recombinant NetB and Generation of Rabbit Anti-rNetB Antisera

The netB gene was PCR amplified and cloned into pENTR/SD/D-TOPO and sub-cloned, in frame, into the expression vector pDest41BA. Protein was purified on a nickel affinity column followed by gel filtration (S200). Peak fractions were pooled and TEV cleaved and reloaded onto a nickel column to remove uncleaved protein and the TEV. Recombinant protein (~1.3 mg) was sent to Chemicon for antibody production (Chemicon-Millipore, Calif., USA). The anti-rNetB antiserum was used in Western blot analysis of *C. perfringens* strains and for neutralization studies.

Native NetB Purification

*C. perfringens* EHE-NE18 was grown in TPG broth until OD600 nm of 0.6. Culture supernatant (3 L) was obtained by centrifugation at 18 000 g for 15 min at 4° C. The supernatant was concentrated 5× using ultrafiltration (Amicon 8400) through a 10 kDa membrane (DIAFLO® YM10-76 mm, Amicon) followed by 40% (w/v) $(NH_4)_2SO_4$ precipitation at 4° C. overnight and separated by centrifugation at 18 000 g for 2 h at 4° C. The precipitate containing the toxin was concentrated 20 times (100 times in total) and dialysed against 10 mM Tris-HCl pH 7.2 over 48 h at 4° C. Proteins were chromatographed in Sepharose Q FF (GE) anion exchange resin with Tris buffer (pH 8.5) and flow through collected.

Example 2

Generation of *C. perfringens* Mutant Strain Lacking the Toxin

DNA manipulations were carried out according to standard techniques. Oligonucleotides used in the construction of the suicide plasmid were AKP60 (SEQ ID NO:7), AKP61 (SEQ ID NO:8), AKP58 (SEQ ID NO:9) and AKP59 (SEQ ID NO:10). All amplified products were cloned into the cloning vector pGEM®-T Easy vector system (Promega) and subsequently subcloned as required. The marked, partial deletion, suicide plasmid, pALK16, was constructed by cloning fragments of the netB gene region on either side of the catP cassette in pALK1 and resulted in a 541 bp deletion of the netB gene. First, a 1490 bp MfeI-SpeI fragment amplified using AKP60 and AKP61 was directionally cloned into the EcoRI-SpeI sites of pALK1, followed by cloning a 1937 bp BamHI-NheI fragment amplified using AKP58 and AKP59 into the BamHI-NheI sites of the resultant plasmid. Finally ermB and oriT amplified from pJIR1457 was blunt end cloned into the SmaI site. The final suicide plasmid pALK16 was introduced into *C. perfringens* strain EHE-NE18 as described previously (Scott and Rood, (1989)). After growth at 37° C. on TSC supplemented with thiamphenicol, colonies were cross-patched onto TSC supplemented with erythromycin to confirm a double crossover event had occurred. The colonies that grew on the appropriate antibiotics were selected for further analysis. Chromosomal DNA was prepared and PCR and Southern blot analysis was used to confirm that the mutants were derived from double crossover events within the netB gene region. The complementation plasmid, pALK20, was constructed by cloning the full length netB gene into the *C. perfringens* shuttle vector pJIR1457 and introduced into both mutants. Complementation was confirmed using erythromycin selection and testing in a cytotoxicity assay. A schematic diagram of the NE18-ΔnetB chromosome region is shown in FIG. 2.

Example 3

Assay of NetB Activity

A cytotoxicity assay was performed on *C. perfringens* EHE-NE18 culture supernatant. LMH cells were cultured until 70% confluence in 24 well plates coated in 0.2% gelatine and grown in EMEM medium at 37° C. Culture supernatant was added to the medium with 2 fold dilution across the plate up to 1:32 and incubated for up to 16 h at 37° C. The LMH cells incubated in the presence of either neat TPG culture media (FIG. 3a); *C. perfringens* EHE-NE18 culture supernatant, 1:16 dilution (FIG. 3b); *C. perfringens* JIR325 non-necrotic enteritis strain 13 culture supernatant, 1:2 dilution (FIG. 3c); or *C. perfringens* NE18-M1 (plc mutant not expressing alpha-toxin) culture supernatant, 1:16 dilution (FIG. 3d). Cytopathic effects (CPE) were observed under a light microscope at 100× magnification.

Normal cells (FIG. 3a) look healthy, however, addition of culture supernatant from a strain producing NetB causes the cells to round-up and die (FIG. 3b). Supernatant from a strain that does not express NetB did not affect the cells (FIG. 3c). Deletion of the alpha-toxin gene does not affect the ability of the culture supernatant to kill cells (FIG. 3d).

Example 4

Complementation of *C. perfringens* NetB Toxin Mutants

The NE18-Deleted netB1 strain (netB negative strain) was complemented with a pALK20 netB complementation plasmid. The complemented strain of *C. perfringens* was then tested for toxin activity. For the cytotoxicity assay, LMH cells were cultured until 70% confluence in 24 well plates coated in 0.2% gelatine and grown in EMEM medium at 37° C. Culture supernatant was added to the medium with 2 fold dilution across the plate up to 1:32 and incubated for up to 16 h at 37° C. The LMH cells were incubated with either: EHE-NE18 culture supernatant, 1:16 dilution (FIG. 4a); NE18-Deleted netB1 culture supernatant, 1:2 dilution (FIG. 4b); NE18-Deleted netB1+pJIR1457 (shuttle plasmid) culture supernatant, 1:2 dilution (FIG. 4c); NE18-Deleted netB1+pALK20

(netB complementation plasmid) culture supernatant, 1:16 dilution (FIG. 4d); neat TPG culture media (FIG. 4e); or column purified recombinant NetB, 1:8 dilution (FIG. 4d).

Deletion of the netB gene abolished killing activity in the cell culture assay. Complementation of the mutant with the gene cloned onto a plasmid restored killing activity. Recombinant NetB protein kills the cultured cells.

Example 5

Quantitative Assay of Cell Killing by Toxin Protein

To determine the ability of NetB to kill cells, a lactate dehydrogenase cytotoxicity assay was performed on LMH cells treated with NetB. The LMH cells were cultured until 70% confluence in 96 well plates coated in 0.2% gelatine and grown in EMEM medium at 37° C. Semi purified NetB from NE18-M1 was added to the medium with 2 fold dilution across the plate up to 1:128 and incubated for 4 h at 37° C. LDH released in the supernatant was measured as an indicator of cytolysis with a Cyto-Tox (Promega) kit and given as a percentage cytotoxicity. Each dilution was done in triplicate and SEM calculated for each dilution (FIG. 5).

Example 6

NetB Mutant Strains in a Chicken Disease Model

Groups of 11 birds were challenged with either the wild-type strain of C. perfringens (NE18) or netB deleted mutants of the strain (NE18-NetB-M1 and NE18-NetB-M2) at 20 and 21 days of age. At 24 days of age the birds were necropsied to score necrotic lesions in the gut. Segments of ileum or jejunum measuring approximately 2-4 cm were collected into 10% neutral sodium phosphate buffered formalin. The small intestine samples were cross-sectioned at 4 mm intervals and segments were processed to paraffin embedded blocks for routine histology and cut at 4-5 µm and stained with haematoxylin and eosin (HE). Histology slides were examined by light microscopy. The guts were scored according to the number of necrotic lesions: 0—No lesions, 1—Thin walled and friable intestines, 2—Focal necrosis or ulceration (1-5 foci), 3—Focal necrosis or ulceration (6-15 foci), 4—Focal necrosis or ulceration (16 or more foci), 5—Patches of necrosis 2-3 cm long, 6—Diffuse necrosis typical of field cases. The wild-type strain showed a significant level of disease whereas neither of the independently isolated mutants showed any sign of disease. We conclude that NetB is a major virulence factor necessary for disease pathogenesis.

TABLE 2

NetB mutant strains have reduced virulence in a chicken disease model.

| | Challenge strain | | |
| --- | --- | --- | --- |
| Bird No. | NE18 | NE18-NetB-M1 | NE18-NetB-M2 |
| 1 | 3 | 0 | 0 |
| 2 | 2 | 0 | 0 |
| 3 | 0 | 0 | 0 |
| 4 | 0 | 0 | 0 |
| 5 | 0 | 0 | 0 |
| 6 | 4 | 0 | 0 |
| 7 | 2 | 0 | 0 |
| 8 | 3 | 0 | 0 |
| 9 | 0 | 0 | 0 |
| 10 | 3 | 0 | 0 |
| 11 | 0 | 0 | 0 |
| Average lesion score | 1.55 | 0 | 0 |
| No. of affected birds in group | 6 | 0 | 0 |
| Weighted score - Av. × No. | 9.3 | 0 | 0 |

Example 7

Survey for Toxin in C. perfringens Strains

PCR survey for Toxin in C. perfringens Strains

The presence of the netB gene in NE and non-NE strains of C. perfringens was investigated by PCR. For each of the C. perfringens strains tested a single colony was suspended in 0.1 ml distilled water and boiled for 10 min and then centrifuged at 10 000 g for 10 min. The supernatants were collected and used as template DNAs in PCR. PCR was performed in a total of 25 µl reaction mixture containing: 1×PCR buffer ($Mg^{2+}$ free); 2.5 mM $MgCl_2$; 0.2 mM dNTP mixture; 2.5 units of Go Taq DNA polymerase (Promega); 50 pM of primers AKP78 and AKP79; and 5 µl template solution. The following conditions were used in the PCR: denaturation at 94° C. for 2 min; 35 cycles of denaturation at 94° C. for 30 s; annealing at 55° C. for 30 s; and extension at 72° C. for 1 min; with the final extension step at 72° C. for 12 min. PCR products were analysed by electrophoresis on 1.5 agarose gels as shown in FIG. 6: a. NE strains; b. Non-NE strains. The 384 bp netB fragment is seen in most C. perfringens strains isolated from necrotic enteritis diseased chickens. The netB specific PCR fragment is not seen in any other strains. This indicated that the presence of the netB gene was a good indicator of C. perfringens virulence in chickens and such an assay can be used to detect potentially virulent strains.

Western Blot Survey for Presence of Toxin in C. Perfringens Strains

C. perfringens strains were grown in pre-boiled TPG broths until OD600 nm ~0.6. Culture supernatant was obtained by centrifugation at 18 000 g for 10 min. Supernatants were separated by SDS-PAGE (NuPAGE® Novex 4-12% Bis-Tris gel, Invitrogen) in MES SDS running buffer (NuPAGE®MES SDS Running Buffer, Invitrogen). Proteins were transferred onto PDVF (Millipore) membrane and probed with rabbit polyclonal anti-rNetB antibody (Chemicon, USA). Blots were developed with ECL Western Blotting kit (Amersham Biosciences, N.J., USA) and results recorded on autoradiographic film as shown in FIG. 7. Brackets indicate NE and non-NE C. perfringens strains. The western blot results confirmed the results of the PCR survey—the gene and protein are present in most NE derived strains but not in non-NE strains. This antibody based detection method is another way to detect potentially virulent strains.

Example 8

Protective Efficacy of Recombinant NetB Subunit Vaccine

The efficacy of recombinant NetB protein (SEQ ID NO:2) when delivered as a subunit vaccine was tested in a vaccination trial.

Vaccination Trial 1193-4

Ross 308 broiler chickens (Aviagen) were vaccinated with 50 μg recombinant NetB as antigen per dose in 0.5 ml Aluminium hydroxide adjuvant. The birds were vaccinated at day 7 and day 14 and challenged at days 20 and 21 with 1.5 ml oral dose of *Clostridium perfringens* strain EHE-NE18. To increase the susceptibility of birds to necrotic enteritis they were feed a high protein diet containing fish meal during the challenge period. Birds were euthanased and necropsied on day 25 to score necrotic enteritis gut lesions.

Lesions were scored according the following scheme:

| | |
|---|---|
| 0 | No lesions |
| 1 | Thin walled and friable intestines |
| 2 | Focal necrosis or ulceration (1-5 foci) |
| 3 | Focal necrosis or ulceration (6-15 foci) |
| 4 | Focal necrosis or ulceration (16 or more foci) |
| 5 | Patches of necrosis 2-3 cm long |
| 6 | Diffuse necrosis typical of field cases |

Results

Average lesion score of chickens vaccinated with NetB recombinant antigen and adjuvant control chickens are provided in Table 3.

TABLE 3

Average lesion score of chickens vaccinated with NetB recombinant antigen.

| Group | Number of birds | Average lesion score | Number affected (Normalised to group of 10) | Average × Number (Normalised to group of 10) |
|---|---|---|---|---|
| Adjuvant control (NE18 challenge) | 27 | 1.74 | 5.93 | 12.37 |
| NetB vaccinated (NE18 challenge) | 18 | 0.21 | 2.1 | 0.46 |

Statistical analysis of the lesion scores using a Mann-Whitney test shows that the difference between the NetB vaccinated group and the Adjuvant control group is statistically significant at greater than 95% confidence.

Example 9

Western Blot Analysis of Sera from Vaccinated Birds

Sera from vaccinated chickens were analysed by Western blot to determine if the chickens produced serum antibodies to NetB protein. 4 μg of recombinant NetB antigen was loaded per well in a polyacrylamide gel and subject to SDS-PAGE. Protein was transferred to PVDF membrane by Western Blot. Sera from vaccinated birds was diluted 1:1000 in 5% skim milk in TBS/0.5% Tween 20 and incubated with the membrane at room temperature for 1 hour. The membrane was washed 3 times with TBS/0.5% Tween 20 and subsequently incubated with goat anti-chicken HRP antibodies (KPL; Cat#14-24-06; Lot #050860) diluted 1:10,000 in 5% skim milk in TBS/0.5% Tween 20 for 1 hour at room temperature. Following incubation the membrane was washed 3 times with TBS/0.5% Tween 20. HRP-labelled secondary antibodies were detected with GE Healthcare ECL Western blotting reagents (Cat#RPN2106) according to manufacturers instructions. The majority of the birds vaccinated with recombinant NetB produced serum antibodies to the NetB protein (FIG. 8) indicating that the vaccine used was capable of inducing a significant immune response to the NetB antigen.

Example 10

Repeat of Vaccination and Challenge Procedure

Vaccination Trial 1219-1

The results produced in trial 1193-4 were tested for reproducibility by repeating the vaccination and challenge procedure with an independently prepared batch of recombinant NetB protein. The results of the repeat trial are provided in Table 4.

TABLE 4

NetB vaccinated group versus Adjuvant control.

| Group | Number of birds | Average lesion score | Number affected | Average × Number (Normalised to group of 10) |
|---|---|---|---|---|
| Adjuvant control (NE18 challenge) | 9 | 2.33 | 7 | 18.1 |
| NetB vaccinated (NE18 challenge) | 11 | 0.64 | 3 | 1.74 |

Statistical analysis of the lesion scores using a Mann-Whitney test showed that the difference between the NetB vaccinated group and the Adjuvant control group was statistically significant at greater than 95% confidence.

Vaccination Trial 1250-1

Using the same vaccination and challenge protocol as the previous trials, the live weights of birds was measured at necropsy. The average weight of each of the negative control, positive control and NetB vaccinated birds are provided in Table 5.

TABLE 5

Live weight of NetB vaccinated birds versus Positive control group.

| Group | Number of birds | Average weight (g) | Std. Dev. (g) |
|---|---|---|---|
| Negative control (No challenge) | 23 | 930 | 105.5 |
| Positive control (NE18 challenge) | 22 | 798 | 107.5 |
| NetB vaccinated (NE18 challenge) | 22 | 914 | 85.7 |

Statistical analysis using an unpaired t-test of the bird weights shows that the weight difference between the NetB vaccinated group and the Positive control group is statistically significant at greater than 99% confidence (P=0.0004685). The vaccinated birds were protected from the restriction in weight gain that affects the unprotected, positive control challenged birds.

Example 11

Protective Efficacy of Alternative NetB Based Vaccines

In vaccination trial 1250-1, a number of alternative vaccines were tested. The alternative vaccines were: Bacterin plus NetB; *E. coli* live vector expressing NetB; and live *C. perfringens* (netB deletant). The alternative vaccines are described below and the live weight of vaccinated birds versus Positive control group are provided in Table 6.

Bacterin Plus NetB

An overnight culture of *C. perfringens* strain EHE-NE18 (400 ml TPG) was prepared. The culture was centrifuged and the cell pellet and supernatant fractions retained. The cell pellet was resuspended in 20 ml of phosphate buffered saline, sonicated to break open the cells and then treated with 0.3% formaldehyde. The supernatant was concentrated by ultrafiltration to a volume of 20 ml and then treated with 0.3% formaldehyde. Equal volumes of the treated cell pellet, supernatant, and adjuvant solutions were combined and recombinant NetB protein was added to a final concentration of 100 mg/ml. 0.5 ml of this formulated vaccine was used subcutaneously per bird per vaccination.

*E. coli* Live Vector Expressing NetB

*E. coli* strain CCEC31rn (as described in WO 2007/025333) was transformed with a plasmid expressing netB from its native promoter. NetB is constitutively expressed from the plasmid. Each bird was orally dosed with 0.5 ml of an overnight culture (Luria broth) at day 2.

Live *C. perfringens* (NetB Deletant)

A netB deleted mutant derivative of *C. perfringens* EHE-NE18 was grown in fluid thioglycolate broth and 0.5 ml was orally inoculated to 2 day old birds.

TABLE 6

Live weight of vaccinated birds versus Positive control group.

| Group | Number of birds | Average weight (g) | Std. Dev. (g) |
|---|---|---|---|
| Bacterin plus NetB | 21 | 895 | 97 |
| *E. coli* live vector expressing NetB | 23 | 877 | 127.5 |
| Live *C. perfringens* (netB deletant) | 23 | 924 | 101 |

Statistical analysis using an unpaired t-test of the bird weights shows that the weight difference between the Bacterin plus NetB vaccinated group and the Positive control group is statistically significant at greater than 99% confidence (P=0.003879), the weight difference between the *E. coli* live vector expressing NetB vaccinated group and the Positive control group is statistically significant at greater than 95% confidence (P=0.0217605) and the weight difference between the live *C. perfringens* strain with deleted netB gene vaccinated group and the Positive control group is statistically significant at greater than 99% confidence (P=0.0003855). These results indicate that the different vaccines can all protect birds from the restriction in weight gain that is seen in the unvaccinated challenged birds.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

The present application claims priority from U.S. 60/942,858, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Altschul, et al. (1997) Nucleic Acids Res, 25:3389-3402.
Awad, et al. (1995) Mol Microbiol, 15:191-202.
Bendtsen, et al. (2004) J Mol Biol, 340:783-795.
Bhugaloo-Vial, et al. (1996) Appl Environ Microbiol, 62:4410-4416.
Boman, (1995) Annu Rev Immunol, 13:61-92.
Boman, (2003) J Intern Med, 254:197-215.
Cardoso, et al. (1996). Virology, 225:293-9.
Cho, et al. (2000) Curr Microbiol, 40:257-263.
Conry, et al. (1994). Cancer Research, 54:1164-68.
Cowen, et al. (1987) Avian Dis, 31:904-906.
Craven, et al. (1999) Avian Dis, 43:484-490.
Ennahar et al. (2000) FEMS Microbiol Rev, 24:85-106.
Fynan, et al. (1993) Proc Natl Acad Sci USA, 90:11478-82.
Gabay, et al (1989) Proc Natl Acad Sci USA, 86:10183.
Gruber et al. (1994) J Immunol 152:5368.
Harayama, (1998) Trends Biotechnol, 16:76-82.
Hollinger et al. (1993) Proc Natl Acad Sci USA 90:6444-6448.
Hood and Jilka (1999) Current Opinions in Biotechnology, 10:382-6.
Ingham, et al. (2003) J Antimicrob Chemother, 51:1365-1371.
Jack, et al. (1995) Microbiol Rev, 59:171-200.
Kaldhusdal, (1999) FEMS Immunol Med Microbiol, 24:337-343.
Kapustra, et al. (1999) FASEB Journal, 13:1796-99.
Kozbor et al. (1985) J Immunol Methods, 81:31-42.
Liu, et al. (2005) Appl Environ Microbiol, 71:6769-6775.
Milstein and Cuello, (1983) Nature, 305:537-539.
Modelska, et al. (1998). Proc Natl Acad Sci USA, 95:2481-85.
Montgomery, et al. (1993) DNA and Cell Biology, 12:777-83.
Morrison (1994) Nature 368:812-13.
Munson and Pollard, (1980) Anal Biochem, 107:220.
Myers and Miller (1989) CABIOS, 4:11-17.
Nahashon, et al. (1994) Poult Sci, 73:1552-1562.
Needleman, and Wunsch, (1970) J Mol Biol, 48:443-453.
Palacios, et al. (2005) J Appl Microbiol, 98:229-237.
Scott and Rood (1989) Gene, 82:327-333.
Songer, et al. (1997) Trends Microbiol, 5:156-161.
Soravia, et al. (1988) FEBS Lett, 228:337-340.
Traunecker et al. (1991) EMBO J, 10:3655-3659.
Tschirdewahn, et al. (1991) Int J Food Microbiol, 14:175-178.
Tutt et al. (1991) J Immunol 147:60.
Vohra and Satyanarayana, (2003) Crit Rev Biotechnol, 23:29-60.
Wahl, et al. (1987) Methods Enzymol, 152:399-407.
Yang, et al. (1997) Vaccine, 15:888-91.

The invention claimed is:

1. A substantially purified and/or recombinant polypeptide, wherein the polypeptide comprises:
   i) the amino acid sequence as provided in SEQ ID NO:2,
   ii) an amino acid sequence which is at least 95% identical to SEQ ID NO:2, and/or
   iii) an antigenic fragment of i) which is at least 10 amino acids in length.

2. The polypeptide of claim 1, wherein the polypeptide has reduced toxin activity compared to a polypeptide having a sequence as shown in SEQ ID NO:2, or the polypeptide is a toxoid.

3. An immunogenic composition comprising an adjuvant and an antigen, wherein the antigen comprises a polypeptide according to claim 1.

4. A feed and/or drink comprising the polypeptide of claim 1.

5. A composition comprising the polypeptide of claim 1.

6. A method of raising an immune response in a subject, the method comprising administering to the subject the polypeptide of claim 1, an immunogenic composition comprising the polypeptide and/or feed and/or drink comprising the polypeptide.

7. The substantially purified and/or recombinant polypeptide of claim 1, wherein the antigenic fragment of i) is at least 20 amino acids in length.

8. The substantially purified and/or recombinant polypeptide of claim 1, wherein the amino acid sequence of ii) is at least 97% identical to SEQ ID NO:2.

9. The substantially purified and/or recombinant polypeptide of claim 1, wherein the amino acid sequence of ii) is at least 99% identical to SEQ ID NO:2.

* * * * *